(12) United States Patent
Gong et al.

(10) Patent No.: US 11,436,720 B2
(45) Date of Patent: Sep. 6, 2022

(54) SYSTEMS AND METHODS FOR GENERATING IMAGE METRIC

(71) Applicant: SHANGHAI UNITED IMAGING INTELLIGENCE CO., LTD., Shanghai (CN)

(72) Inventors: Zaiwen Gong, Shanghai (CN); Hengze Zhan, Shanghai (CN); Jie-Zhi Cheng, Shanghai (CN); Yiqiang Zhan, Shanghai (CN); Jibing Wu, Shanghai (CN); Xiang Sean Zhou, Shanghai (CN)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 142 days.

(21) Appl. No.: 16/729,249

(22) Filed: Dec. 27, 2019

(65) Prior Publication Data
US 2020/0211186 A1     Jul. 2, 2020

(30) Foreign Application Priority Data

Dec. 28, 2018  (CN) .......................... 201811626384.2
Dec. 29, 2018  (CN) ........................ 201811632060.X
Dec. 29, 2018  (CN) ......................... 201811634593.1

(51) Int. Cl.
*G06T 7/00* (2017.01)
*G06T 7/11* (2017.01)
(Continued)

(52) U.S. Cl.
CPC .......... *G06T 7/0012* (2013.01); *A61B 5/0033* (2013.01); *G06N 20/00* (2019.01);
(Continued)

(58) Field of Classification Search
CPC . G06T 2207/20081; G06T 2207/20084; G06T 2207/20132; G06T 2207/30048;
(Continued)

(56) References Cited

U.S. PATENT DOCUMENTS 5,600,574 A * 2/1997 Reitan ................ H04N 1/00015
                                                        702/185
7,488,107 B2 * 2/2009 Tubbs .................... A61B 6/583
                                                        378/207
(Continued)

FOREIGN PATENT DOCUMENTS

CN       103745470 A       4/2014
CN       105997119 A       10/2016
(Continued)

OTHER PUBLICATIONS

First Office Action in Chinese Application No. 201811634593.1 dated May 22, 2020, 14 pages.
(Continued)

*Primary Examiner* — Katrina R Fujita
(74) *Attorney, Agent, or Firm* — Metis IP LLC

(57) ABSTRACT

The present disclosure may provide a method. The method may include processing an image of a subject using a detection model to generate one or more detection results corresponding to one or more objects in the image; and generating an image metric of the image based on the one or more detection results corresponding to the one or more objects.

20 Claims, 18 Drawing Sheets

(51) Int. Cl.
  *G06N 20/00* (2019.01)
  *A61B 5/00* (2006.01)
(52) U.S. Cl.
  CPC ........... *G06T 7/11* (2017.01); *A61B 2576/023* (2013.01); *G06T 2207/20081* (2013.01); *G06T 2207/20084* (2013.01); *G06T 2207/30048* (2013.01); *G06T 2207/30061* (2013.01); *G06T 2207/30168* (2013.01)
(58) Field of Classification Search
  CPC . G06T 2207/33061; G06T 2207/30168; G06T 7/0012; G06T 7/11; A61B 5/0033; A61B 5/05; A61B 2576/023; G06N 3/0454; G06N 3/84; G06N 20/00
  See application file for complete search history.

(56) References Cited

U.S. PATENT DOCUMENTS

| | | | |
|---|---|---|---|
| 9,595,090 | B2 | 3/2017 | Bovik et al. |
| 2004/0122708 | A1 | 6/2004 | Avinash et al. |
| 2007/0047789 | A1* | 3/2007 | Dewaele ............... G06T 7/168 382/128 |
| 2008/0226147 | A1* | 9/2008 | Hargrove ............... G06T 5/50 382/128 |
| 2009/0041325 | A1* | 2/2009 | Luo ............... G06T 7/0012 382/132 |
| 2015/0313569 | A1* | 11/2015 | Stevens ............... A61B 6/544 378/8 |
| 2017/0007196 | A1* | 1/2017 | Don ............... A61B 6/032 |
| 2017/0224302 | A1* | 8/2017 | Von Berg ............. A61B 6/5217 |
| 2017/0337681 | A1* | 11/2017 | Lure ............... G06T 7/13 |
| 2018/0061054 | A1 | 3/2018 | Abraham et al. |
| 2018/0300539 | A1 | 10/2018 | Guan et al. |
| 2019/0392577 | A1* | 12/2019 | Cadieu ............... G06T 7/0014 |
| 2020/0054306 | A1* | 2/2020 | Mehanian ............. A61B 8/5207 |
| 2020/0093455 | A1* | 3/2020 | Wang .................. G16H 50/70 |
| 2020/0167930 | A1* | 5/2020 | Wang .................. G06T 7/0012 |

FOREIGN PATENT DOCUMENTS

| | | |
|---|---|---|
| CN | 107203989 A | 9/2017 |
| CN | 104424629 B | 1/2018 |
| CN | 107578416 A | 1/2018 |
| CN | 107730505 A | 2/2018 |
| CN | 107784647 A | 3/2018 |
| CN | 107808377 A | 3/2018 |
| CN | 107909581 A | 4/2018 |
| CN | 108288271 A | 7/2018 |
| CN | 108364017 A | 8/2018 |
| CN | 108460774 A | 8/2018 |
| CN | 108537784 A | 9/2018 |
| CN | 108550150 A | 9/2018 |
| CN | 108596198 A | 9/2018 |
| CN | 108648172 A | 10/2018 |
| CN | 108648182 A | 10/2018 |
| CN | 108682015 A | 10/2018 |
| CN | 108806776 A | 11/2018 |
| CN | 109009110 A | 12/2018 |
| CN | 109035283 A | 12/2018 |
| CN | 109035284 A | 12/2018 |
| CN | 109598734 A | 4/2019 |
| CN | 109727251 A | 5/2019 |
| CN | 109859168 A | 6/2019 |

OTHER PUBLICATIONS

First Office Action in Chinese Application No. 201811632060.X dated Jun. 3, 2020, 19 pages.
First Office Action in Chinese Application No. 201811626384.2 dated Jun. 30, 2020, 18 pages.
Zhang, Li, Quality Control and Quality Assurance of DR Photographic Image, China Continuing Medical Education, 9 (21): 63-65, 2017.
E. Nasr-Esfahani et al., Vessel Extraction in X-Ray Angiograms Using Deep Learning, IEEE 2016 38th Annual International Conference of the IEEE Engineering in Medicine and Biology Society (EMBC), 38: 643-646, 2016.
Deng, Jincheng et al., Application of Deep Convolution Neural Network in Radiotherapy Planning Image Segmentation, Chinese Journal of Medical Physics, 35(6): 621-627, 2018.
Liu, Yan et al., An Automated Calculation of Cardiothoracic Ratio on Chest Radiography, Chinese Journal of Biomedical Engineering, 2009, 5 pages.
Kevin G. et al., Pathological pulmonary lobe segmentation from CT images using progressive holistically nested neural networks and random walker, Deep Learning in Medical Image Analysis and Multimodal Learning for Clinical Decision Support, 2017, 8 pages.
International Search Report in PCT/CN2019/129553 dated Apr. 17, 2020, 5 pages.
Written Opinion in PCT/CN2019/129553 dated Apr. 17, 2020, 6 pages.
The Second Office Action in Chinese Application No. 201811634593.1 dated March 30, 2021, 16 pages
Serkan Kiranyaz et al., Particle Swarm Optimization, Multidimensional Particle Swarm Optimization for Machine Learning and Pattern Recognition, 45-80, 2014.

* cited by examiner

SYSTEMS AND METHODS FOR GENERATING IMAGE METRIC

CROSS-REFERENCE TO RELATED APPLICATIONS

This application claims priority to Chinese Patent Application No. 201811626384.2 filed on Dec. 28, 2018, Chinese Patent Application No. 201811634593.1 filed on Dec. 29, 2018, and Chinese Patent Application No. 201811632060.X filed on Dec. 29, 2018, the entire contents of each of which are hereby incorporated by reference.

TECHNICAL FIELD

The present disclosure generally relates to systems and methods for generating an image metric of a medical image, and more specifically relates to systems and methods for generating the image metric based on machine learning techniques.

BACKGROUND

A medical image provides a visual representation of the interior and/or exterior of a subject (e.g., a patient) for various purposes including, e.g., clinical diagnosis. The quality of the medical image may affect one or more aspects of the clinical diagnosis including, e.g., accuracy, efficiency, which in turn may affect the accuracy, efficacy, etc., of subsequent measures (e.g., treatment planned and/or performed) on the basis of the clinical diagnosis. If the quality of the medical image is insufficient for the clinical diagnosis, the probability of misdiagnosis of a pathological condition reflected in the medical image may increase. In some cases, an operator (e.g., a doctor) manually assesses the quality of the medical image, which is time-consuming and the accuracy of the assessment is affected by the experience of the operator.

Currently, the clinical diagnosis includes determining whether the medical image reflects at least one pathological condition of the subject. In some cases, the operator may manually determine the pathological condition(s), which is time-consuming. For example, the operator uses a ruler and a pen to manually draw the contour of the lung of a subject. If the lung has pneumothorax, the operator also uses the ruler and the pen to manually draw the part of pneumothorax. In some cases, the pathological condition is determined based on a current detection algorithm (e.g., an edge detection algorithm, a fuzzy c-mean (FCM) algorithm), which only allows partially automated determination of a pathological condition to some limited extent and/or under limited circumstances, e.g., due to the complexity of the detection algorithm. Thus, it is desirable to provide systems and methods for automated assessment of the quality of a medical image and/or diagnosis of a pathological condition based on the medical image with improved efficiency and/or accuracy.

SUMMARY

In one aspect of the present disclosure, a system may be provided. The system may include at least one storage device including a set of instructions; at least one processor in communication with the at least one storage device, wherein when executing the set of instructions, the at least one processor may be configured to cause the system to perform operations including: processing an image of a subject using a detection model to generate one or more detection results corresponding to one or more objects in the image; and generating an image metric of the image based on the one or more detection results corresponding to the one or more objects.

In a second aspect of the present disclosure, a method may be provided. The method may be implemented on a computing device having at least one processor, at least one computer-readable storage medium, and a communication platform connected to a network. The method may include: processing an image of a subject using a detection model to generate one or more detection results corresponding to one or more objects in the image; and generating an image metric of the image based on the one or more detection results corresponding to the one or more objects.

In a third aspect of the present disclosure, a non-transitory computer readable medium may be provided. The non-transitory computer readable medium may include instructions being executed by at least one processor, causing the at least one processor to implement a method. The method may include: processing an image using a detection model to generate one or more detection results corresponding to one or more objects in the image; and generating an image metric of the image based on the one or more detection results corresponding to the one or more objects.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Figure 2:
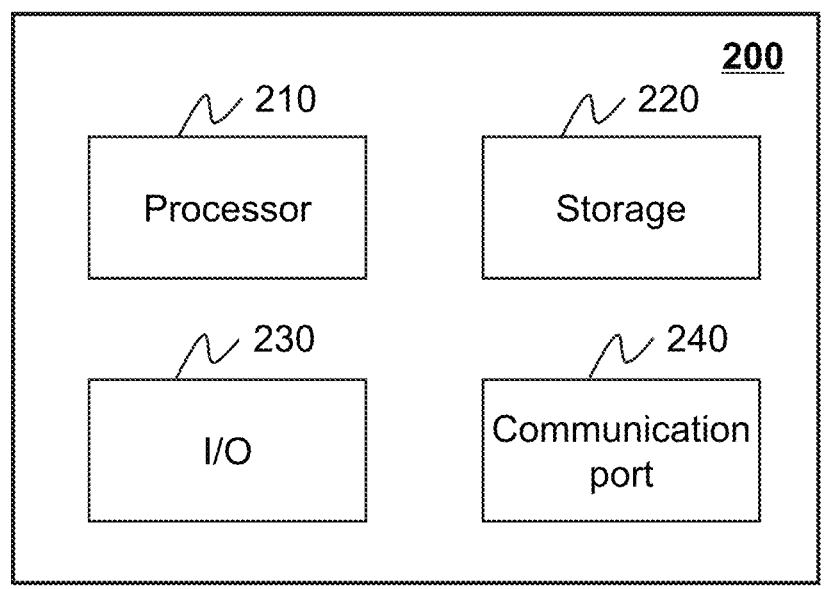
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, an X-ray imaging system, a magnetic resonance imaging (MRI) system, a computed tomography (CT) system, a positron emission tomography (PET) system, an ultrasound system or the like, or any combination thereof. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), image-guided radiotherapy (IGRT), etc. The image-guided radiotherapy (IGRT) may include a treatment device and an imaging device. The treatment device may include a linear accelerator, a cyclotron, a synchrotron, etc., configured to perform radiotherapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

As used herein, a representation of an object (e.g., a patient, a subject, or a portion thereof) in an image may be referred to the object for brevity. For instance, a representation of an organ or tissue (e.g., the heart, the liver, a lung, etc., of a patient) in an image may be referred to as the organ or tissue for brevity. An image including a representation of an object may be referred to as an image of the object or an image including the object for brevity. As used herein, an operation on a representation of an object in an image may be referred to as an operation on the object for brevity. For instance, a segmentation of a portion of an image including a representation of an organ or tissue (e.g., the heart, the liver, a lung, etc., of a patient) from the image may be referred to as a segmentation of the organ or tissue for brevity.

An aspect of the present disclosure relates to systems and methods for generating an image metric of an image. As used herein, the image metric may include the quality of the image and/or a clinical finding corresponding to one or more objects in the image. The image may be automatically processed using a detection model to generate one or more detection results corresponding to the object(s) in the image. The image metric may be determined based on the detection result(s). For illustration purposes, the image metric may be determined by comparing the detection result(s) with a first condition regarding whether the quality of the image meets an imaging standard and/or a second condition regarding whether the object(s) are in a normal (or healthy) condition. Merely by way of example, the image may include a chest image. The chest image may include a representation of the interior of the chest of a subject (e.g., a patient). The object(s) in the image may include a lung, a spine, a scapula, a heart, a foreign object, an abnormal part, or a portion thereof, or the like, or any combination thereof. The clinical finding may regard cardiac hypertrophy, pneumothorax, pleural effusion, pneumonia, tumor, or the like, or any combination thereof.

In some embodiments of the present disclosure, the detection model may be generated by training a preliminary detection model based on a plurality of training images. The preliminary detection model may be a deep learning model. The deep learning model may have multiple layers to learn training detection results of the training images using a set of algorithms.

Compared to manual image metric determination or image metric determination based on other detection algorithms, the system and method according to embodiments disclosed herein, using the detection model, may achieve automated image processing to assess the quality of an image, generate one or more detection results regarding object(s) represented in an image whose quality meets a imaging standard, and/or determine, based on the one or more detection results, a clinical finding regarding the object(s) with improved efficiency, improved accuracy, reduced cross-operator variance, etc.

In some embodiments of the present disclosure, a first part of the training images may be obtained from a storage device. A second part of the training images may be generated or synthesized by transforming at least a portion of the first part of the training images. By synthesizing training samples based on available training samples, more training samples may become available for training the detection model and/or the volume and/or diversity of the training samples may be improved. By improving the volume and/or diversity of the training images, accordingly, the detection model so trained may be more robust and enjoy wider applicability.

It should be noted a chest image is referred to in describing various embodiments merely as an example. The methods and systems disclosed herein may be applied in the processing of images of other parts of other subjects. Exemplary parts of the subject may include a head, a neck, an abdomen, a leg, or the like, or any combination thereof. For example, if the image includes the abdomen, the object(s) in the image may include a liver, a spleen, a stomach, a colon, an appendix, a bladder, a kidney, or the like, or any combination thereof. The clinical finding may regard gastroenteritis, appendicitis, gastritis, hydronephrosis, tumor, or the like, or any combination thereof.

Figure 1:
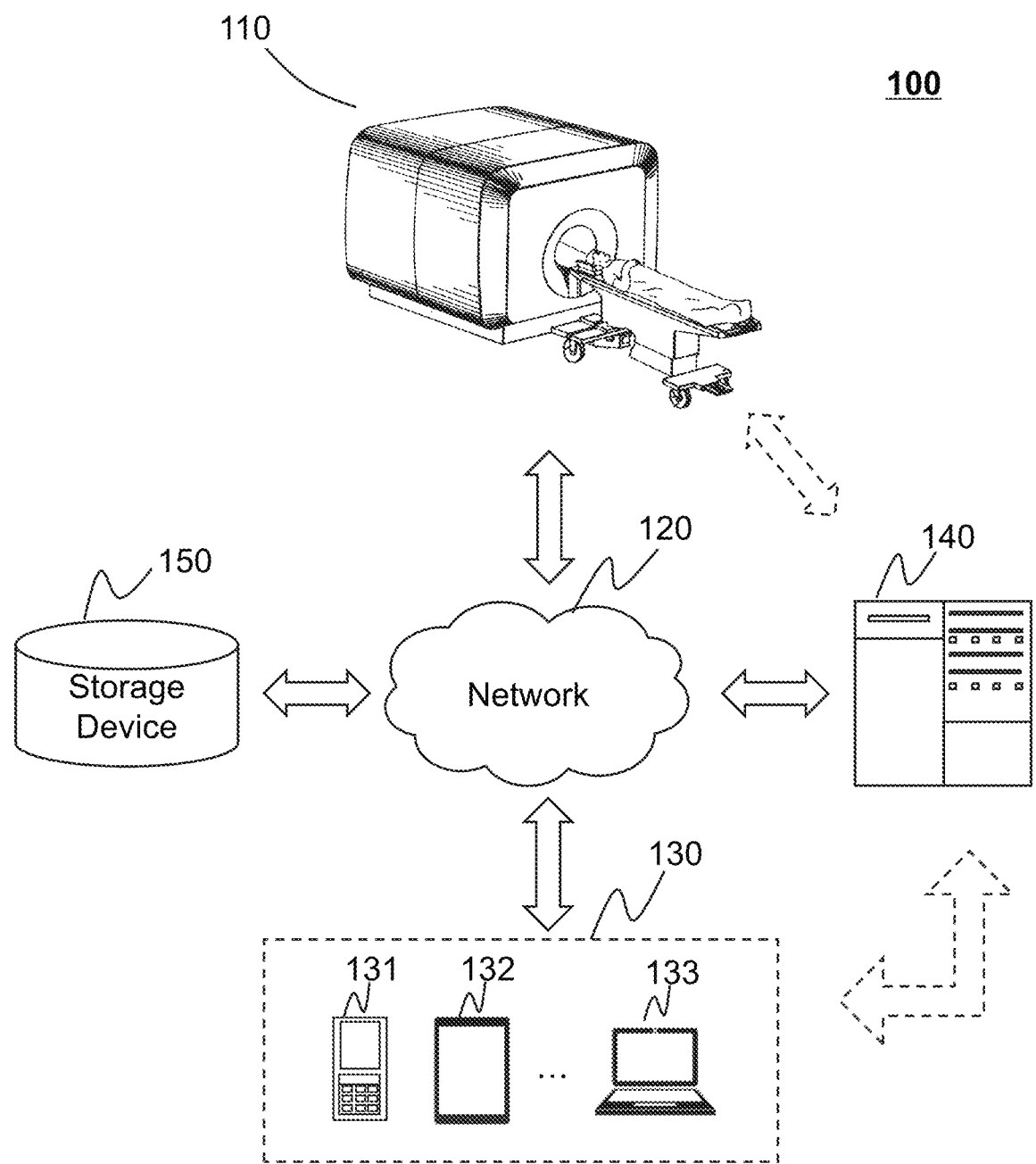
FIG. 1 is a schematic diagram illustrating an exemplary image processing system according to some embodiments of the present disclosure.

FIG. 1 is a schematic diagram illustrating an exemplary image processing system 100 according to some embodiments of the present disclosure. As illustrated, the image processing system 100 may include an imaging device 110, a network 120, a terminal 130, a processing device 140, and a storage device 150. The components of the image processing system 100 may be connected in one or more of various ways. Mere by way of example, as illustrated in FIG. 1, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The imaging device 110 may scan a subject located within its detection space and generate a plurality of data relating to the subject. In the present disclosure, "subject" and "object" are used interchangeably. The subject may include a biological subject (e.g., a human, an animal), a non-biological subject (e.g., a phantom), etc. In some embodiments, the subject may include a specific part, organ, and/or tissue of the subject. For example, the subject may include chest, head, brain, neck, body, shoulder, arm, thorax, cardiac, stomach, blood vessel, soft tissue, knee, feet, or the like, or any combination thereof. For example, the imaging device 110 may include a chest X-ray (CXR) device.

The network 120 may include any suitable network that can facilitate the exchange of information and/or data for the image processing system 100. In some embodiments, one or more components of the image processing system 100 (e.g., the imaging device 110, the terminal 130, the processing device 140, or the storage device 150) may communicate information and/or data with one or more other components of the image processing system 100 via the network 120. For example, the processing device 140 may obtain an image (e.g., a chest image) acquired by the imaging device 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the image processing system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the imaging device 110 and/or the processing device 140. In some embodiments, the terminal 130 may operate the imaging device 110 and/or the processing device 140 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

Figure 4A:
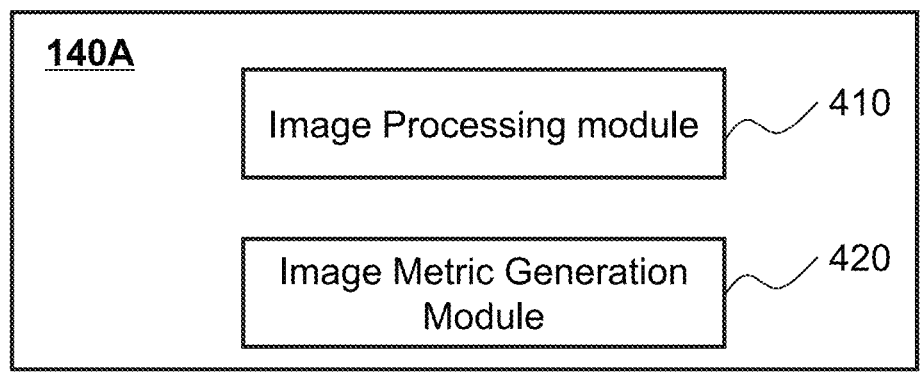
FIGS. 4A and 4B provide schematic block diagrams illustrating exemplary processing devices according to some embodiments of the present disclosure.
Figure 4B:
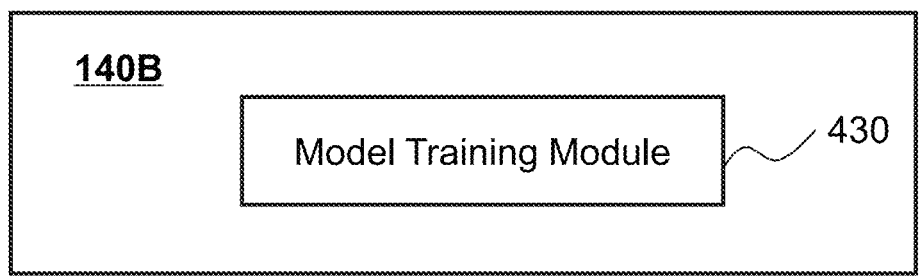

The processing device 140 may process data and/or information obtained from the imaging device 110, the terminal 130, and/or the storage device 150. For example, the processing device 140 may process a plurality of training images and generate (including maintenance or updating) a detection mode by training a preliminary detection model based on thereof. As another example, the processing device 140 may apply the detection model to process an image of a subject to generate one or more detection results corresponding to one or more objects in the image. Further, the processing device 140 may generate an image metric of the image based on the one or more detection results. In some embodiments, the training of the detection model and the application of the detection model may be performed by the same processing device. In some embodiments, the training of the detection model may be performed by a processing device (e.g., a processing device 140B as illustrated in FIG. 4B), while the application of the detection model may be performed on a different processing device (e.g., a processing device 140A as illustrated in FIG. 4A). In some embodiments, the training of the detection model may be performed by a processing device of a system different from the image processing system 100 or a server different from the processing device on which the application of the detection model is performed. For example, the training of the detection model may be performed by a first system of a vendor who provides and/or maintains such a detection model, while the application of the detection model may be performed on a second system of a client of the vendor. In some embodiments, the application of the detection model may be performed online in response to a request for processing an image. In some embodiments, the training of the detection model may be performed offline.

In some embodiments, the processing device 140 may be a single server or a server group. The server group may be centralized, or distributed. In some embodiments, the processing device 140 may be local or remote. For example, the processing device 140 may access information and/or data stored in or acquired by the imaging device 110, the terminal 130, and/or the storage device 150 via the network 120. As another example, the processing device 140 may be directly connected to the imaging device 110 (as illustrated by the bidirectional arrow in dashed lines connecting the processing device 140 and the imaging device 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data and/or instructions. In some embodiments, the storage device 150 may store data obtained from the imaging device 110, the terminal 130 and/or the processing device 140. For example, the processing device 140 may process an image of a subject using a detection model to generate one or more detection results corresponding to one or more objects in the image, and then the detection result(s) may be stored in the storage device 150 for further use or processing. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the image processing system 100 (e.g., the imaging device 110, the processing device 140, the terminal 130, etc.). One or more components of the image processing system 100 may access the data or instructions stored in the storage device 150 via the network 120. In some embodiments, the storage device 150 may be directly connected to or communicate with one or more components of the image processing system 100 (e.g., the imaging device 110, the processing device 140, the terminal 130, etc.). In some embodiments, the storage device 150 may be part of the processing device 140.

In some embodiments, the image processing system 100 may further include one or more power supplies (not shown in FIG. 1) connected to one or more components of the image processing system 100 (e.g., the imaging device 110, the processing device 140, the terminal 130, the storage device 150, etc.).

FIG. 2 is a schematic diagram illustrating exemplary hardware and/or software components of a computing device on which the processing device 140 may be implemented according to some embodiments of the present disclosure. As illustrated in FIG. 2, the computing device 200 may include a processor 210, a storage 220, the input/output (I/O) 230, and a communication port 240.

The processor 210 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 210 may obtain, from the storage device 150 and/or the terminal 130, a detection model. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors. For example, if in the present disclosure the processor of the computing device 200 executes both operations A and B, it should be understood that operations A and step B may also be performed by two different processors jointly or separately in the computing device 200 (e.g., a first processor executes operation A and a second processor executes operation B, or the first and second processors jointly execute operations A and B).

The storage 220 may store data/information obtained from the imaging device 110, the terminal 130, the storage device 150, or any other component of the Image processing system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for processing an image using a detection model to generate one or more detection results corresponding to one or more objects in the image.

The I/O 230 may input or output signals, data, or information. In some embodiments, the I/O 230 may enable user interaction with the processing device 140. In some embodiments, the I/O 230 may include the input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) of the processing device 140 may input data related to a subject (e.g., a patient) that is being/to be imaged/scanned through the I/O 230. The data related to the subject may include identification information (e.g., the name, age, gender, medical history, contract information, physical examination result, etc.) and/or the test information including the nature of the scan that must be performed. The user may also input parameters needed for the operation of the imaging device 110, such as image contrast and/or ratio, a region of interest (ROI), or the like, or any combination thereof. The I/O 230 may also display an image (or videos) generated based on the imaging/scan data.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
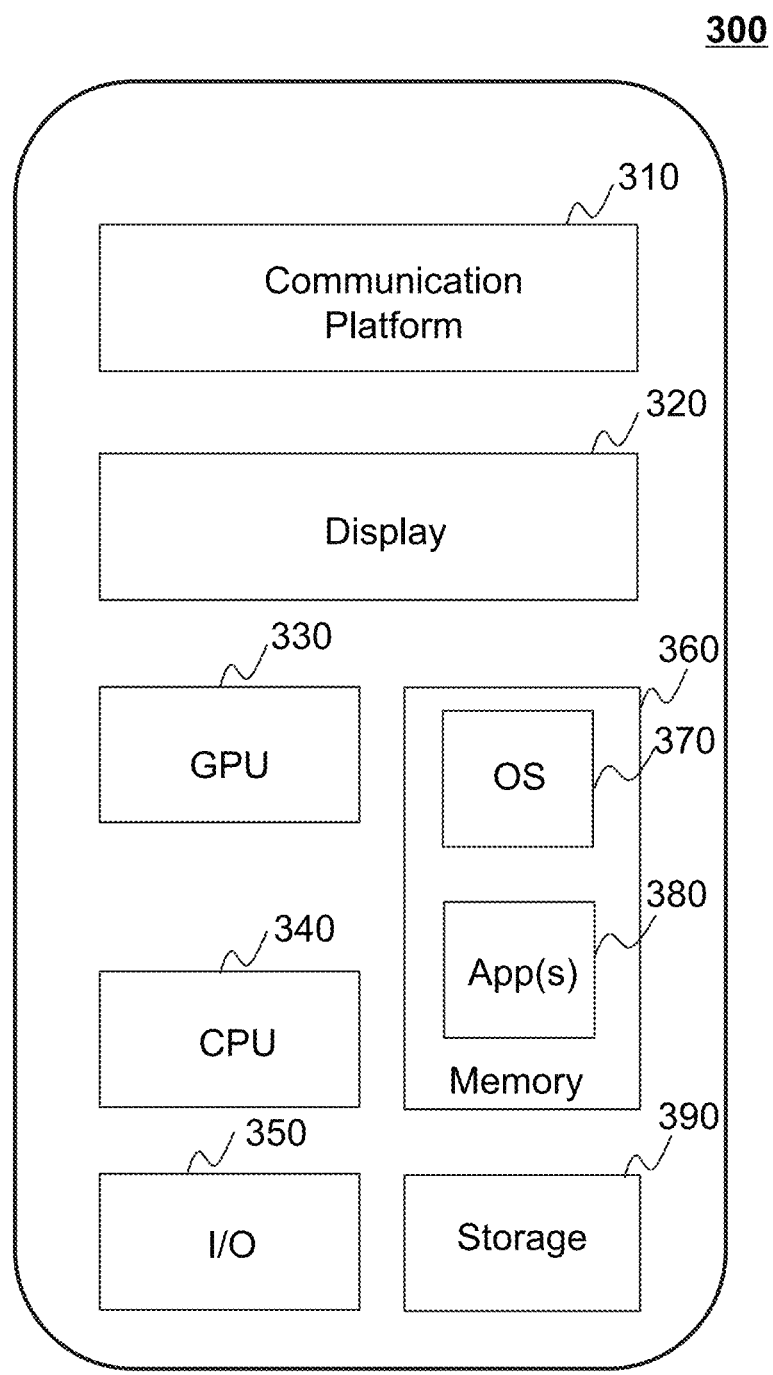
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the Image processing system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

FIGS. 4A and 4B provide schematic block diagrams illustrating exemplary processing devices 140A and 140B according to some embodiments of the present disclosure. In some embodiments, the processing device 140A may be configured to generate an image metric of an image based on a detection model. The processing device 140B may be configured to generate the detection model by training a preliminary model based on a plurality of training images. For illustration purposes, the processing devices 140A and 140B may respectively be implemented on the computing device 200 as illustrated in FIG. 2 or the CPU 340 as illustrated in FIG. 3. The processing device 140A and the processing device 140B may be both implemented on the processing device 140 as illustrated in FIG. 1. In some embodiments, the processing device 140A may be implemented on the processing device 140 as illustrated in FIG. 1, while the processing device 140B may be implemented on a processing device of a manufacturer or vendor who provides and/or maintains such a detection model.

The processing device 140A may include an image processing module 410 and an image metric generation module 420. The processing device 140B may include a model training module 430.

The image processing module 410 may be configured to process an image of a subject using a detection model to generate one or more detection results corresponding to one or more objects in the image. In some embodiments, the image may include a chest image. As used herein, a chest image may include a representation of the interior of the chest of a subject (e.g., a patient). For illustration purposes, the image may include an image of a frontal chest. Exemplary objects in the image may include a lung, a spine, a scapula, a heart, a foreign object, a heart, an abnormal part, or a portion thereof, or the like, or any combination thereof. As used herein, a foreign object refers to an object from the outside of a subject.

In some embodiments, the detection model may be configured to determine the detection result(s) corresponding to the object(s) in the image. For illustration purposes, the image processing module 410 may generate the detection result(s) by inputting the image into the detection model. For example, a detection result corresponding to an object may include a position of the object in the image, a bounding box of the object in the image, a contour of the object in the image, a region of the image that corresponds to the object in the image, a dimension of the object in the image, or the like, or any combination thereof. Taking a chest image as an example, exemplary detection result(s) may include a first detection result corresponding to a scapula, a second detection result corresponding to a lung, a third detection result corresponding to a foreign object, a fourth detection result corresponding to a spine, a fifth detection result corresponding to a heart, a sixth detection result corresponding to an abnormal part, or the like, or any combination thereof.

In some embodiments, the image processing module 410 may also preprocess the image, and generate the detection result(s) based on the preprocessed image using the detection model. For example, the image processing module 410 may input the preprocessed image into the detection model and generate the detection result(s). In some embodiments, the image processing module 410 may preprocess the image by performing at least one of normalizing the image, adjusting the size of the image, rotating the image, flipping the image, cropping the image, changing a contrast ratio-of the image, removing artifact and/or noise of the image, etc. For illustration purposes, the normalization of the image may include min-max normalization, 0-1 normalization, etc.

The image metric generation module 420 may be configured to generate an image metric of the image based on the one or more detection results corresponding to the one or more objects. In some embodiments, the image metric of the image may include the quality of the image and/or a clinical finding corresponding to the object(s) in the image. As used herein, a clinical finding may indicate a physiological condition of each of one or more objects in an image. For example, the physiological condition may include a normal (or healthy) condition and an abnormal (unhealthy or pathological) condition of the object.

In some embodiments, the quality of the image may be characterized by an image quality classification. In some embodiments, the image quality classification may include a first level and a second level. If the image belongs to the first level, the image can be used to generate a clinical finding. If the image belongs to the second level, the image may not be used to generate a clinical finding. In some embodiments, the image quality classification may also include an intermediate level. If the image belongs to the intermediate level, the image can be used to generate a clinical finding.

In some embodiments, the image metric generation module 420 may determine whether the one or more detection results corresponding to the one or more objects satisfy a condition. Further, the image metric generation module 420 may determine the image quality classification based on the determination result. In some embodiments, the image metric generation module 420 may determine that the image belongs to the first level. For instance, in response to determining that the detection result(s) satisfies the condition, the image metric generation module 420 may determine that the image belongs to the first level.

In some embodiments, the image metric generation module 420 may determine that the image belongs to the second level. For instance, in response to determining that the detection result(s) fails to satisfy the condition, the image metric generation module 420 may determine that the image belongs to the second level. In response to determining that the second detection result fails to satisfy the condition, the image metric generation module 420 may determine that the image belongs to the second level.

In some embodiments, the image metric generation module 420 may determine that the image belongs to the intermediate level. For instance, in response to determining that the second detection result and the third detection result satisfy the condition, and that at least one of the fourth detection result or the first detection result fails to satisfy the condition, the image metric generation module 420 may determine that the image belongs to the intermediate level. In response to determining that the second detection result satisfies the condition, and that at least one of the fourth detection result or the first detection result fails to satisfy the condition, the image metric generation module 420 may determine that the image belongs to the intermediate level.

Merely by way of example, in response to determining a first item that the first detection result, the second detection result, and the fourth detection result satisfy the condition, a second item that the third detection result fails to satisfy the condition, and a third item that the third detection result is located outside the second detection result (one or more of the three items being satisfied), the image metric generation module 420 may determine that the image belongs to the intermediate level. As another example, in response to determining that the second detection result, that the third detection result fails to satisfy the condition, and that the third detection result is located outside the second detection result, the image metric generation module 420 may determine that the image belongs to the intermediate level.

Merely by way of example, in response to determining a first item that the first detection result, the second detection result, and the fourth detection result satisfy the condition, a second item that the third detection result fails to satisfy the condition, and a third item that the third detection result is inside the second detection result (one or more of the three items being satisfied), the image metric generation module 420 may determine that the image belongs to the second level. As another example, in response to determining that the second detection result, that the third detection result fails to satisfy the condition, and that the third detection result is located inside the second detection result, the image metric generation module 420 may determine that the image belongs to the intermediate level.

For illustration purposes, the detection result(s) may include the second detection result and the third detection result. In response to determining a first item that the second detection result satisfies the condition, a second item that the third detection result fails to satisfy the condition, and a third item that the third detection result is located outside the second detection result (one or more of the three items being satisfied), the image metric generation module 420 may determine that the image belongs to the intermediate level. In response to determining a first item that the second detection result satisfies the condition, a second item that the third detection result fails to satisfy the condition, and a third item that the third detection result is located inside the second detection result (one or more of the three items being satisfied), the image metric generation module 420 may determine that the image belongs to the second level.

In some embodiments, the image metric generation module 420 may allocate different weights to the different detection results. In some embodiments, the clinical finding may include at least one pathological condition of the object(s). In some embodiments, the image metric generation module 420 may allocate different weights to the different detection results based on the pathological condition(s). For example, if the pathological condition(s) relates to the lung, the image metric generation module 420 may allocate a relatively high weight to the second detection result.

In some embodiments, the image metric generation module 420 may generate an explanation why the image belongs to the intermediate level or the second level. In some embodiments, the explanation may include at least one of the parameter(s) that fails to satisfy the condition, the name of an object whose detection result fails to satisfy the condition, or the like, or a combination thereof.

In some embodiments, the image metric generation module 420 may generate a clinical finding based on the one or more detection results corresponding to the one or more objects. The clinical finding may indicate the physiological condition of the object(s) in the image. For example, the physiological condition may include the normal (or healthy) condition and the abnormal (unhealthy or pathological) condition of the object. For illustration purposes, the clinical finding may include at least one parameter of the object(s), at least one pathological condition of the object(s), a severity degree of a pathological condition, or the like, or any combination thereof. Taking a chest image as an example, the parameter(s) may include the width of the heart, the width of the lung, a ratio between the width of the heart to the width of the lung, a ratio of a volume of the abnormal part to a volume of the lung, or the like, or any combination thereof. Exemplary pathological conditions may include cardiac hypertrophy, pneumothorax, pleural effusion, pneumonia, tumor, or the like, or any combination thereof.

In some embodiments, the image metric generation module 420 may determine a fourth ratio of the width of the fifth detection result to the second detection result based on the fifth detection result and the second detection result. The image metric generation module 420 may compare the fourth ratio with the fourth ratio threshold to determine whether the pathological condition of cardiac hypertrophy exists. In response to determining that the fourth ratio exceeds the fourth ratio threshold, the image metric generation module 420 may determine the clinical finding that the pathological condition of cardiac hypertrophy exists. In response to determining that the fourth ratio is smaller than the fourth ratio threshold, the image metric generation module 420 may determine the pathological condition of cardiac hypertrophy is absent.

In some embodiments, if the object(s) include the abnormal part, the image metric generation module 420 may determine a pathological condition of the abnormal part based on the sixth detection result corresponding to the abnormal part. For example, the pathological condition of the abnormal part may include pneumothorax, pleural effusion, pneumonia, tumor, or the like, or any combination thereof.

If the pathological condition of the abnormal part includes pneumothorax, the image metric generation module 420 may determine that the clinical finding includes the pathological condition of pneumothorax. In response to determining that the fifth ratio exceeds a fifth ratio threshold (e.g., 40%), the image metric generation module 420 may determine that the pathological condition of high-risk pneumothorax exists. In response to determining that the fifth ratio is smaller than a sixth ratio threshold (e.g., 10%), the image metric generation module 420 may determine that the pathological condition of self-healing pneumothorax exists.

If the pathological condition of the abnormal part includes pleural effusion, the image metric generation module 420 may determine that the clinical finding includes the pathological condition of pleural effusion. In response to determining that the sixth ratio exceeds a seventh ratio threshold (e.g., 40%), the image metric generation module 420 may determine that a pathological condition of high-risk pleural effusion exists. In some embodiments, the clinical finding may also include the sixth ratio. In response to determining that the sixth ratio is smaller than an eighth ratio threshold (e.g., 10%), the image metric generation module 420 may determine that a pathological condition of self-healing pleural effusion exists.

The model training module 430 may be configured to determine the detection model by training a preliminary detection model using a plurality of training images on the deep learning platform. For illustration purposes, the model training module 430 may train the preliminary model using a supervised learning technique or a semi-supervised learning technique. In some embodiments, the detection model may be generated by iteratively updating one or more training parameters of the preliminary detection model based on the training samples.

In some embodiments, the detection model may include a plurality of detection sub-models. The model training module 430 may generate the detection model by separately training a preliminary detection sub-model. For instance, the model training module 430 may train each individual detection sub-model based on a preliminary detection sub-model and sample images (also referred to as "training image"). The training of the preliminary detection sub-model may terminate when a termination condition is deemed satisfied. The detection model may be generated by combining the separately trained detection sub-models.

Alternatively, the model training module 430 may generate the detection model by jointly training a plurality of preliminary detection sub-models. For instance, the model training module 430 may perform an iterative training process. In each iteration, the model training module 430 may jointly train the plurality of preliminary or intermediate detection sub-models using a sample image, and a termination condition relating to the plurality of preliminary or intermediate detection sub-models may be assessed to determine whether a further iteration needs to be performed. As used herein, an intermediate detection sub-model may be one obtained based on a corresponding preliminary detection sub-model in the training process.

The modules in the processing device 140A or the processing device 140B may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140A or the processing device 140B may further include a storage module (not shown in FIG. 5). The storage module may be configured to store data generated during any process performed by any component of the processing device 140A or the processing device 140B. As another example, each of the components of the processing device 140A or the processing device 140B may include a storage device. Additionally or alternatively, the components of the processing device 140A or the processing device 140B may share a common storage device. In some embodiments, the processing devices 140A and 140B may be integrated to a single processing device to perform the functions thereof. Merely by way of example, the processing device 140A and the processing device 140B may be implemented on a processing device configured to generate the detection model and generate the image metric of the image based on the detection model.

Figure 5:
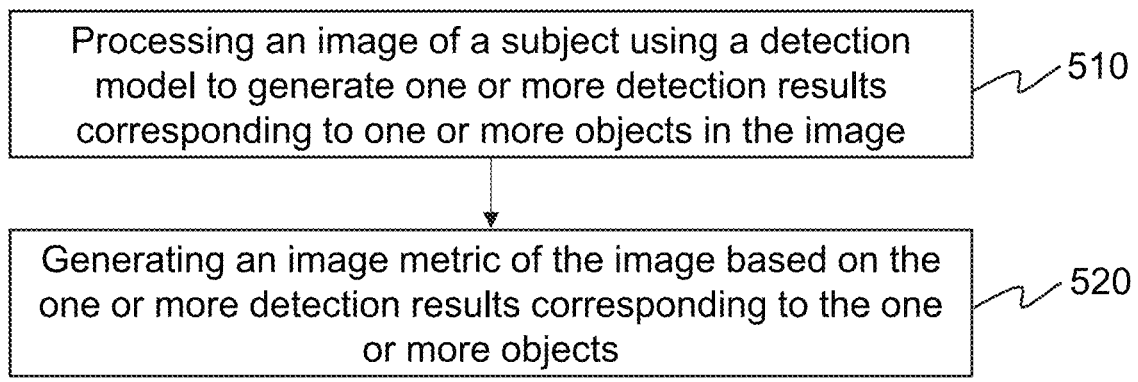
FIG. 5 is a flowchart illustrating an exemplary process for generating an image metric of an image based on a detection model according to some embodiments of the present disclosure.

FIG. 5 is a flowchart illustrating an exemplary process for generating an image metric of an image based on a detection model according to some embodiments of the present disclosure. In some embodiments, the process 500 may be implemented in the image processing system 100 illustrated in FIG. 1. For example, the process 500 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing devices 140A and/or 140B illustrated in FIGS. 4A-4B). The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 140A (e.g., the image processing module 410) may process an image of a subject using a detection model to generate one or more detection results corresponding to one or more objects in the image. In some embodiments, the processing device 140A may obtain the image from a component (e.g., the imaging device 110, the terminal 130, the storage device 150) of the imaging processing system 100. For example, the image may be acquired by the imaging device 110. The processing device 140A may obtain the image directly from the imaging device 110, or from a storage device (e.g., storage device 150) where an image acquired by the imaging device 110 (or another imaging device) in advance is stored. In some embodiments, the processing device 140A may obtain the image from a source external to the image processing system 100.

For example, the image may include, a two-dimensional (2D) image, a three-dimensional (3D) image, a four-dimensional (4D) image, etc. As another example, the image may include an X-ray image, a magnetic resonance (MR) image (e.g., a streaming MR image, a volumetric MR image, a cine MR image), a computed tomography (CT) image (e.g., a cone-beam CT (CBCT) image), a positron emission tomography (PET) image (e.g., a single-photon emission computed tomography (SPECT) image), a functional MR image (e.g., an fMR image, a dynamic contrast-enhanced MR (DCE-MR) image, a diffusion MR image), a fluoroscopic image, an ultrasound image, a radiotherapy portal image, or the like, or any combination thereof.

In some embodiments, the image may include a chest image. As used herein, a chest image may include a representation of the interior of the chest of a subject (e.g., a patient). For illustration purposes, the image may include an image of a frontal chest. Exemplary objects in the image may include a lung, a spine, a scapula, a heart, a foreign object, a heart, an abnormal part, or a portion thereof, or the like, or any combination thereof. As used herein, a foreign object refers to an object from the outside of a subject. For illustration purposes, the foreign object may include an object worn by the subject. Exemplary foreign objects may include a button, a necklace, or the like, or any combination thereof. As used herein, an abnormal part may refer to a part of the subject that is in an abnormal (unhealthy or pathological) condition. For illustration purposes, the abnormal part may be caused by a disease or pathological condition, e.g., pneumothorax, pleural effusion, pneumonia, tumor, etc. In some embodiments, at least one of the object(s) in the image may be in the abnormal condition. Alternatively, the object(s) in the image may be in a normal (or healthy) condition.

In some embodiments, the detection model may be configured to determine the detection result(s) corresponding to the object(s) in the image. For illustration purposes, the processing device 140A may generate the detection result(s) by inputting the image into the detection model. For example, a detection result corresponding to an object may include a position of the object in the image, a bounding box of the object in the image, a contour of the object in the image, a region of the image that corresponds to the object in the image, a dimension of the object in the image, or the like, or any combination thereof. Taking a chest image as an example, exemplary detection result(s) may include a first detection result corresponding to a scapula, a second detection result corresponding to a lung, a third detection result corresponding to a foreign object, a fourth detection result corresponding to a spine, a fifth detection result corresponding to a heart, a sixth detection result corresponding to an abnormal part, or the like, or any combination thereof.

In some embodiments, the detection model may be a single model configured to determine the detection result(s) corresponding to the object(s) in the image. For example, the detection model may include a model configured to determine detection results corresponding to the lung, the spine, the scapula, the foreign object, the heart, and the abnormal part. As another example, the detection model may include a model configured to determine detection result(s) corresponding to at least one of the lung, the spine, the scapula, or the foreign object. As a further example, the detection model may include a model configured to determine detection results corresponding to the lung and the heart. As still a further example, the detection model may include a model configured to determine detection results corresponding to the lung and the abnormal part.

In some embodiments, the detection model may include multiple detection sub-models. Each of the multiple detection sub-models may be configured to determine detection results corresponding to at least one of the object(s). For example, the detection model may include a plurality of detection sub-models each of which is configured to determine a detection result corresponding to at least one of the lung, the spine, the scapula, or the foreign object. As another example, the detection model may include a detection sub-model configured to determine detection results corresponding to the lung and the heart. As a further example, the detection model may include a detection sub-model configured to determine detection results corresponding to the lung and the abnormal part. As still a further example, each of the multiple detection sub-models may be configured to determine a detection result corresponding to one of the object(s). The detection model may include a lung detection sub-model, a spine detection sub-model, a scapula detection sub-model, a foreign object detection sub-model, an abnormal part detection sub-model, a heart detection sub-model, or the like, or any combination thereof. The scapula detection sub-model configured to determine a first detection result corresponding to the scapula. The lung detection sub-model may be configured to determine a second detection result corresponding to the lung. The foreign object detection sub-model may be configured to determine a third detection result corresponding to the foreign object. The spine detection sub-model may be configured to determine a fourth detection result corresponding to the spine. The heart detection sub-model may be configured to determine a fifth detection result corresponding to the heart. The abnormal part detection sub-model may be configured to determine a sixth detection result corresponding to the abnormal part.

In some embodiments, the detection model may include a deep learning model, e.g., a convolutional neural network (CNN) model, a support vector machine (SVM) model, etc. For example, the detection model (e.g., the detection sub-models) may include a volumetric network (V-net) model, a LinkNet model, a fully convolutional DenseNet (FC-DenseNet) model, a faster region-based convolutional neural network (Faster-RCNN) model, a RetinaNet model, a you-only-look-once (YOLO) network model, a region-based convolutional neural network (RCNN) model, a single shot multibox (SSD) network model, a single-shot refinement neural network (RefineDet) model, or the like, or any combination thereof. In some embodiments, the types of the detection sub-models of the detection model may be the same or different. For example, the lung detection sub-model and the heart detection sub-model may be the V-net model.

In some embodiments, the detection model may be determined based on a deep learning platform. The deep learning platform may be used for building the deep learning model, e.g., the detection model. In some embodiments, the deep learning platform may be trained and/or maintained on the image processing system 100, or a part thereof, or on a system external to the image processing system 100. In some embodiments, the detection model may be determined by the image processing system 100 (e.g., the processing device 140B, a storage device (the storage device 150, the storage 220, the storage 390)) or a third party (e.g., an external device). In some embodiments, the image processing system 100 may determine and/or update the detection model offline and store the detection model in the storage device. In some embodiments, the detection model may be determined and/or updated (or maintained) by, e.g., the manufacturer of an imaging device (e.g., the imaging device 110) or a vendor. For instance, the manufacturer or the vendor may load the detection model into the image processing system 100 or a part thereof (e.g., the storage device 150, the processing device 140A) before or during the installation of the imaging device and/or the processing device 140A, and maintain or update detection model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new detection model) or a part of a model that substitutes or supplements a corresponding part of the model.

In some embodiments, the processing device 140B may determine the detection model by training a preliminary detection model using a plurality of training images on the deep learning platform. For illustration purposes, the processing device 140B may train the preliminary model using a supervised learning technique or a semi-supervised learning technique. In some embodiments, the detection model may be generated by iteratively updating one or more training parameters of the preliminary detection model based on the training samples.

In some embodiments, the detection model may include a plurality of detection sub-models. The processing device 140B may generate the detection model by separately training a preliminary detection sub-model. For instance, each individual detection sub-model may be trained based on a preliminary detection sub-model and sample images (also referred to as "training images"). The training of the preliminary detection sub-model may terminate when a termination condition is deemed satisfied. The detection model may be generated by combining the separately trained detection sub-models. An exemplary termination condition may relate to an objective function (e.g., a loss function, a total variation function) relating to the preliminary or an intermediate detection sub-model, a certain number or count of iterations that have been performed, or the like, or a combination thereof. As used herein, an intermediate detection sub-model may be one obtained based on a corresponding preliminary detection sub-model in the training process. For instance, the training of a first preliminary detection sub-model may terminate after a first termination condition is deemed satisfied, while the training of a second preliminary detection sub-model may terminate after a second termination condition is deemed satisfied, in which the first termination condition is different from the second termination condition. The training of different detection sub-models may be performed in parallel or sequentially. Separately or individually trained sub-models may be combined to form the detection model. The training of two different detection sub-models may be independent from each other.

Alternatively, the processing device 140B may generate the detection model by jointly training a plurality of preliminary detection sub-models. For instance, the processing device 140B may perform an iterative training process. In each iteration, the plurality of preliminary or intermediate detection sub-models are jointly trained using a sample image, and a termination condition relating to the plurality of preliminary or intermediate detection sub-models may be assessed to determine whether a further iteration needs to be performed. As used herein, an intermediate detection sub-model may be one obtained based on a corresponding preliminary detection sub-model in the training process. The corresponding preliminary detection sub-model with one or more updated training parameters in one iteration may be referred to as the intermediate detection sub-model. An exemplary termination condition may relate to an objective function (e.g., a loss function, a total variation function) relating to the plurality of preliminary or intermediate detection sub-models, a certain number or count of iterations that have been performed, or the like, or a combination thereof. The training of the plurality of detection sub-models may be completed at the same time. The jointly trained plurality of detection sub-models may be combined to form the detection model.

Merely by way of example, the detection sub-models may include a lung detection model configured to determine a detection result corresponding to a lung and an abnormal part detection model configured to determine a detection result corresponding to an abnormal part. The processing device 140B may generate a single model configured to determine detection results corresponding to the lung and the abnormal part. More descriptions of generating the detection model may be found elsewhere in the present disclosure. See, e.g., FIG. 8 and the descriptions thereof.

In some embodiments, the processing device 140A may also preprocess the image, and generate the detection result(s) based on the preprocessed image using the detection model. For example, the processing device 140A may input the preprocessed image into the detection model and generate the detection result(s). In some embodiments, the processing device 140A may preprocess the image by performing at least one of normalizing the image, adjusting the size of the image, rotating the image, flipping the image, cropping the image, changing a contrast ratio of the image, removing artifact and/or noise of the image, etc. For example, the processing device 140A may adjust the size (e.g., 128×128) of the image to a size (e.g., 64×64) that the detection model is configured to process. As another example, the processing device 140A may crop or rotate the image randomly. As a further example, the processing device 140A may flip the image. It should be noted the sequence of the preprocessing may be non-limiting. For example, the processing device 140A may first preprocess the image by adjusting the size of the image and then rotating the image. Alternatively, the processing device 140A may first preprocess the image by rotating the image and then adjusting the size of the image.

For illustration purposes, the normalization of the image may include min-max normalization, 0-1 normalization, etc. In some embodiments, the processing device 140A may rank gray values of a plurality of elements in the image, e.g., in descending order or ascending order. For example, an element in the image may include a pixel in the image if the image is two-dimensional (2D), a voxel in the image if the image is three-dimensional (3D), etc. Further, the processing device 140A may normalize the gray values according to Equation (1):

$$x'=(x-x_1)/(x_2-x_1), \quad (1)$$

where x' denotes a normalized gray value of one of the plurality of elements, and x denotes a gray value of the element. In some embodiments, $x_1$ is the minimum value of the gray values of the plurality of elements, and $x_2$ is the maximum value of the gray values of the plurality of elements.

In some embodiments, the processing device 140A may designate a first gray value of a first element ranked at a first specified place as $x_1$, and a second gray value of a second element ranked at a second specified place as $x_2$. For instance, among the elements of the image, $x_1$ is the gray value of an element of the image that exceeds or is equal to the gray values of a first percentage (e.g., 5%) of elements of the image, and $x_2$ is the gray value that exceeds or is equal to the gray values of a second percentage (e.g., 95%) of elements of the image; in other words, among the elements of the image, the gray values of 95% of the elements may exceed or be equal to $x_1$, and the gray values of 5% of the elements may exceed or be equal to $x_2$.

In some embodiments, the processing device 140A may determine a first group and a second group of the elements, and $x_1$ and $x_2$ may be an element among elements in the first group and the second group, respectively. In some embodiments, the processing device 140A may assign an element to the first group or the second group based on the gray value of the element. For example, gray values of elements assigned to the first group may be within a first range of the ranked elements. Gray values of elements assigned to the second group may be within a second range of the ranked elements. For example, the processing device 140A may rank the elements based on the gray values in an order (e.g., descending order or ascending order); the processing device 140A may assign elements ranking at 0%-10% to the first group and elements ranking at 90%-100% to the second group; $x_1$ may be an element ranking at 5%, and $x_2$ may be an element ranking at 95%. As another example, the processing device 140A may rank the elements of an image based on the gray values in an order and assign elements ranking 0%-20% to the first group and elements ranking at 80%-100% to the second group; $x_1$ may be an element ranking at 10%, and $x_2$ may be an element ranking at 90%. In some embodiments, the processing device 140A may further standardize the normalized gray values according to Equation (2):

$$x^* = (x-\mu)/\sigma \qquad (2)$$

where $x^*$ denotes the gray value of one of the plurality of elements after standardization, x denotes the normalized gray value of the element, $\mu$ denotes an average value of the gray values of the plurality of elements, and $\sigma$ denotes a standard deviation of the gray values of the plurality of elements.

In 520, the processing device 140A (e.g., the image metric generation module 420) may generate an image metric of the image based on the one or more detection results corresponding to the one or more objects. In some embodiments, the image metric of the image may include the quality of the image and/or a clinical finding corresponding to the object(s) in the image. As used herein, a clinical finding may indicate a physiological condition of each of one or more objects in an image. For example, the physiological condition may include a normal (or healthy) condition and an abnormal (unhealthy or pathological) condition of the object.

In some embodiments, the quality of the image may be characterized by an image quality classification. The image quality classification may indicate a confidence level for generating the clinical finding using the image. For illustration purposes, the greater the confidence level is, the more reliable the clinical finding generated based on the image may be. In some embodiments, the image quality classification may include a first level and a second level. The first level may indicate sufficient confidence for generating the clinical finding using the image and/or that the image satisfies a first imaging standard. If the image belongs to the first level, the image can be used to generate a clinical finding. The second level may indicate little confidence if used to generate the clinical finding and/or that the image fails to satisfy a second imaging standard. In some embodiments, the first imaging standard may be the same as or different from the second imaging standard. As used herein, an imaging standard is used to assess whether an image is suitable to be used as an input or basis to make a clinical finding or diagnosis, e.g., by a processing device (e.g., using the detection model disclosed herein) or by a user. Factors that may negatively impact the quality of an image (and therefore its suitability to be used as an input or basis to make a clinical finding or diagnosis) may include one or more of image contrast, image resolution, artifact, whether an image includes a complete representation of a portion of a subject that is of clinical interest, the location of the representation of such a portion of a subject of clinical interest in the image, whether an image includes a representation of a portion of a subject or a foreign object that is of little or no clinical interest, whether a representation of a portion of a subject or a foreign object that is of little or no clinical interest in the image occupies too much of the image (evaluated in terms of, e.g., area ratio, location of such a representation), or the like, or a combination thereof.

In some embodiments, if the image belongs to the second level, the image may not be used to generate a clinical finding. In some embodiments, the image quality classification may also include an intermediate level. A confidence level corresponding to the intermediate level may be between the confidence level corresponding to the first level and the confidence level corresponding to the second level. In some embodiments, if the image belongs to the intermediate level, the image can be used to generate a clinical finding.

In some embodiments, the processing device 140A may determine the image quality classification and/or confidence level based on the detection result(s) and a condition. In some embodiments, the condition may relate to an imaging standard (e.g., the first imaging standard, the second imaging standard, etc., referred to elsewhere in the present disclosure) for an image including the object(s). For illustration purposes, the imaging standard may relate to the existence of a foreign object, whether an abnormal part is inside a lung, whether at least a part of a scapula is inside a lung in the image, whether the spine is located in a center region of the image, whether the lung field is completely depicted in the image, or the like, or any combination thereof. For example, the imaging standard for an image of object(s) includes one or more of: the image lacking any foreign object, the scapula of the image being outside the lung, the spine being located in a center region of the image, or the lung field being completely depicted in the image. As a further example, the imaging standard for an image of object(s) includes all of: the image lacking any foreign object, the scapula of the image being outside the lung, the spine being located in a center region of the image, and the lung field being completely depicted in the image.

In some embodiments, if the image belongs to the first level, the detection result(s) may satisfy the condition and be deemed suitable to be used as a basis for a clinical finding. If the image belongs to the intermediate level or the second level, a part of the detection result(s) may satisfy the condition. More descriptions of generating the image quality classification may be found elsewhere in the present disclosure. See, e.g., FIG. 6 and the descriptions thereof.

As illustrated above, the clinical finding may indicate the physiological condition of each of one or more objects in the image. For example, the physiological condition may include the normal (or healthy) condition and the abnormal (unhealthy or pathological) condition of the object. For illustration purposes, the clinical finding may include at least one parameter of the object(s), at least one pathological condition of the object(s), a severity degree of a pathological condition, or the like, or any combination thereof. Taking a chest image as an example, the parameter(s) may include the width of the heart, the width of the lung, a ratio between the width of the heart to the width of the lung, a ratio of a volume of the abnormal part to a volume of the lung, or the like, or any combination thereof. Exemplary pathological conditions may include cardiac hypertrophy, pneumothorax, pleural effusion, pneumonia, tumor, or the like, or any combination thereof. In some embodiments, the processing device 140A may generate the clinical finding based on the detection result(s). More descriptions of generating the clinical finding may be found elsewhere in the present disclosure. See, e.g., FIG. 7 and the descriptions thereof.

In some embodiments, before generating the clinical finding, the processing device 140A may determine the quality of the image. The processing device 140A may generate the clinical finding if the image is deemed suitable to be used as a basis to generate the clinical finding. In some embodiments, the processing device 140A may determine the quality of the image based on the process for determining the image quality classification as illustrated above. For example, if the image is deemed belonging to the first level or the intermediate level, the processing device 140A may use the image to generate the clinical finding. As another example, if the image is deemed belonging to the second level, the processing device 140A may discard the image. A new image may be obtained by rescanning or retrieved for generating the clinical finding.

In some embodiments, the processing device 140A may also generate a notification regarding the image metric of the image. For example, the notification may include the image quality classification of the image, the parameter(s) of the object, the pathological condition of the object(s), or the severity degree of the pathological condition, or the like, or any combination thereof. In some embodiments, the notification may be in the form of texts, voices, images, digits, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
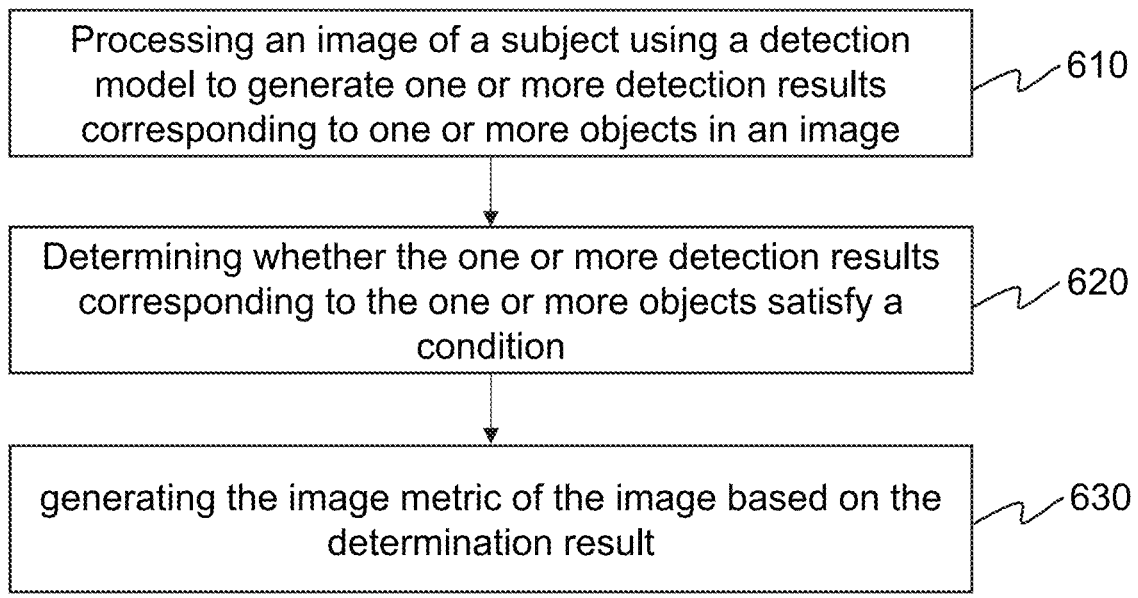
FIG. 6 is a flowchart illustrating an exemplary process for generating an image metric of an image based on a detection model according to some embodiments of the present disclosure.

FIG. 6 is a flowchart illustrating an exemplary process for generating an image metric of an image based on a detection model according to some embodiments of the present disclosure. In some embodiments, the process 600 may be implemented in the image processing system 100 illustrated in FIG. 1. For example, the process 600 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing devices 140A and/or 140B illustrated in FIGS. 4A-4B). The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 140A (e.g., the image processing module 410) may process an image of a subject using a detection model to generate one or more detection results corresponding to one or more objects in an image. In some embodiments, the processing device 140A may obtain the image from a component (e.g., the imaging device 110, the terminal 130, the storage device 150) of the imaging processing system 100. For example, the image may be acquired by the imaging device 110. The processing device 140A may obtain the image directly from the imaging device 110, or from a storage device (e.g., the storage device 150) where an image acquired by the imaging device 110 (or another imaging device) in advance is stored. In some embodiments, the processing device 140A may obtain the image from a source external to the image processing system 100.

As illustrated in connection with operation 510, the image may include a chest image. For illustration purposes, the image may include an image of a frontal chest. Exemplary objects in the image may include a lung, a spine, a scapula, a heart, a foreign object, an abnormal part, or a portion thereof, in the image. Exemplary detection result(s) may include a first detection result corresponding to a scapula, a second detection result corresponding to a lung, a third detection result corresponding to a foreign object, a fourth detection result corresponding to a spine, a fifth detection result corresponding to a heart, a sixth detection result corresponding to an abnormal part, or the like, or any combination thereof. For example, a detection result corresponding to an object may include a position of the object, a bounding box of the object, a contour of the object, a region of the object, a dimension of the object, or the like, or any combination thereof.

In some embodiments, the processing device 140A may preprocess the image, and generate the detection result(s) based on the preprocessed image using the detection model. For example, the processing device 140A may input the preprocessed image into the detection model and generate the detection result(s). More descriptions of preprocessing the image may be found elsewhere in the present disclosure. See, e.g., operation 510 and the descriptions thereof.

In 620, the processing device 140A (e.g., the image metric generation module 420) may determine whether the one or more detection results corresponding to the one or more objects satisfy a condition. As described in connection with 520, the condition may relate to an imaging standard for an image including the object(s) if the image can be used to generate the clinical finding. For illustration purposes, the imaging standard may relate to the existence of a foreign object, whether an abnormal part is inside a lung, whether at least a part of a scapula is inside a lung in the image, whether the spine is located in a center region of the image, whether the lung field is completely depicted in the image, or the like, or any combination thereof. For example, the imaging standard for an image of object(s) includes one or more of: the image lacking any foreign object, the scapula of the image being outside the lung, the spine being located in a center region of the image, or the lung field being completely depicted in the image. As a further example, the imaging standard for an image of object(s) includes all of: the image lacking any foreign object, the scapula of the image being outside of the lung, the spine being located in a center region of the image, and the lung field being completely depicted in the image. In some embodiments, the imaging standard may relate to personal information of the subject, e.g., medical history, age, height, gender, weight, etc. Different subjects with different personal information may corresponding to different imaging standards. The processing device 140A may set the imaging standard according to personal information of the subject.

Accordingly, the condition may include or relate to the one or more detection results of the subject. The condition may include one or more items defined based on the one or more detection results. An exemplary item of the condition may include or relate to a second ratio of a third area of an overlapping region between the first detection result and the second detection result to a fourth area of the second detection result being smaller than a second ratio threshold. An exemplary item of the condition may include or relate to a second ratio of a third area of an overlapping region between the first detection result and the second detection result to a fourth area of the second detection result being smaller than a second ratio threshold. An exemplary item of the condition may include or relate to a third ratio of the third area to the second area being smaller than a third ratio threshold. An exemplary item of the condition may include or relate to the second detection result being located within a range of the image. An exemplary item of the condition may include or relate to a confidence value of the third detection result being smaller than a confidence value threshold. An exemplary item of the condition may include or relate to an offset value of the fourth detection result relative to a reference line being smaller than an offset threshold. An exemplary item of the condition may include or relate to one or more of the exemplary items described above, or the like. For illustration purposes, the processing device 140A may determine the confidence value of the foreign object based on the detection model using a non-maximum suppression algorithm. In some embodiments, similar to the imaging standard, the condition may relate to the personal information of the subject, e.g., medical history, age, height, gender, weight, etc. Different subjects with different personal information may corresponding to different conditions. The processing device 140A may set the condition according to the personal information of the subject.

As illustrated, a first detection result may be that the detection result corresponding to the scapula. A second detection result may be that the detection result corresponding to the lung. A third detection result may be that the detection result corresponding to the foreign object. A fourth detection result may be that the detection result corresponding to the spine. A fifth detection result may be that the detection result corresponding to the heart. A sixth detection result may be that the detection result corresponding to the abnormal part.

In some embodiments, the processing device 140A may determine whether the first detection result satisfies the condition based on the detection result(s). In some embodiments, the processing device 140A may determine whether the first ratio of a first area of the first detection result to a second area of a portion of the image that corresponds to the chest is smaller than a ratio threshold, indicating whether the area of the detected scapula in an image (the first detection result) is sufficiently small relative to the second area of the portion of the image that corresponds to the chest. In response to determining that the first ratio is smaller than the ratio threshold, the processing device 140A may determine the first detection result satisfies the condition. In response to determining that the first ratio exceeds the ratio threshold, the processing device 140A may determine the first detection result fails to satisfy the condition. It should be noted that, in response to determining that the first ratio is equal to the ratio threshold, the processing device 140A may determine that the first detection result satisfies the condition or not. For example, in response to determining that the first ratio is equal to the ratio threshold, the processing device 140A may determine that the first detection result satisfies the condition. As another example, in response to determining that the first ratio is equal to the ratio threshold, the processing device 140A may determine that the first detection result fails to satisfy the condition.

In some embodiments, the ratio threshold may be set according to default settings of the image processing system 100 or by a user. In some embodiments, the ratio threshold may be determined based on a plurality of sample images and the detection model. In some embodiments, the ratio threshold may be determined offline by the processing device 140A, the processing device 140B, or a processing device other than the processing device 140A and the processing device 140B. Merely by way of example, the following descriptions are provided in which the processing device 140B is configured to determine the ratio threshold.

The plurality of sample images may have been analyzed and labeled as satisfying the imaging standard or not. The prior analysis and labeling may be performed by, e.g., one or more users, one or more processing devices, etc. The prior labeling of a sample image may be referred to as an actual determination result of the sample image. The processing device 140B may determine a first sample detection result corresponding to a sample scapula in each sample image based on the detection model. The first sample detection result corresponding to the sample scapula may be similar to or the same as the first detection result corresponding to the scapula as illustrated in operation 510, and is not repeated here. The processing device 140B may also determine first sample ratios of the sample images based on the first sample detection results. The processing device 140B may set a candidate ratio threshold. The processing device 140B may generate a determination result of each of the sample image based on the candidate ratio threshold and the first sample detection results. If a first sample ratio of a sample image is smaller than the candidate ratio threshold, the processing device 140B may deem that the sample image meets an imaging standard with respect to the first sample detection result of the sample image. If a first sample ratio exceeds the candidate ratio threshold, the processing device 140B may deem that the sample image fails to meet the imaging standard with respect to the first sample detection result of the sample image. The processing device 140B may determine an accuracy associated with the determination results by comparing the determination results with the corresponding actual determination results. For illustration purposes, if a determination result of a sample image is consistent with an actual determination result of the sample image, the processing device 140B may determine that the determination result of the sample image is accurate. If the determination result of the sample image is different from the actual determination result of the sample image, the processing device 140B may determine that the determination result of the sample image is inaccurate. In some embodiments, if the accuracy rate associated with the determination results based on a candidate ratio threshold exceeds a preset rate, the processing device 140B may designate the candidate ratio threshold as the ratio threshold. If the accuracy rate associated with the determination results based on a candidate ratio threshold is smaller than the preset rate, the processing device 140B may adjust the candidate ratio threshold and repeat the process for determining the ratio threshold based on the candidate ratio threshold as already described. For example, among 500 sample images available to determine the ratio threshold, based on a candidate ratio threshold (e.g., a candidate threshold within the range of 0.009-0.028), 400 sample images meet the imaging standard with respect to the scapula, and 100 sample images fails to meet the imaging standard with respect to the scapula, and the accuracy rate associated with determination results of the 500 sample images exceeds 90%, the processing device 140B may designate a value in the range of 0.009-0.028 as the ratio threshold. The value may be set according to default settings of the image processing system 100 or by a user. In some embodiments, the processing device 140 may set the value based on one or more accuracy rates determined based on one or more values within the range of 0.009-0.028 and the plurality of sample images. For example, the processing device 140 may designate a value within the range corresponding to the maximum accuracy rate as the ratio threshold.

In some embodiments, the processing device 140A may determine whether the second ratio of the third area of the overlapping region between the first detection result and the second detection result to the fourth area of the second detection result is smaller than the second ratio threshold, indicating whether the overlapping region between the scapula and the lung in the image is sufficiently small relative to the area of the lung in the image. In response to determining that the second ratio is smaller than the second ratio threshold, the processing device 140A may determine the first detection result satisfies the condition. In response to determining that the second ratio exceeds the second ratio threshold, the processing device 140A may determine the first detection result fails to satisfy the condition. In some embodiments, a process for determining the second ratio threshold may be the same as or similar to the process for determining the ratio threshold as already described, and is not repeated here. In some embodiments, the second ratio threshold may be set according to default settings of the image processing system 100 or by a user. It should be noted that, in response to determining that the second ratio is equal to the second ratio threshold, the processing device 140A may determine that the first detection result satisfies the condition or not. For example, in response to determining that the second ratio is equal to the second ratio threshold, the processing device 140A may determine that the first detection result satisfies the condition. As another example, in response to determining that the second ratio is equal to the second ratio threshold, the processing device 140A may determine that the first detection result fails to satisfy the condition.

In some embodiments, the processing device 140A may determine whether the third ratio of the third area of the overlapping region between the first detection result and the second detection result to the second area of the portion of the image that corresponds to the chest is smaller than the third ratio threshold, indicating whether the overlapping region between the scapula and the lung is sufficiently small relative to the portion of the image that corresponds to the chest. In response to determining that the third ratio is smaller than the third ratio threshold, the processing device 140A may determine the first detection result satisfies the condition. In response to determining that the third ratio exceeds the third ratio threshold, the processing device 140A may determine the first detection result fails to satisfy the condition. In some embodiments, a process for determining the third ratio threshold may be the same as or similar to the process for determining the ratio threshold as illustrated below, and is not repeated here. In some embodiments, the third ratio threshold may be set according to default settings of the image processing system 100 or by a user. It should be noted that, in response to determining that the third ratio is equal to the third ratio threshold, the processing device 140A may determine that the first detection result satisfies the condition or not. For example, in response to determining that the third ratio is equal to the third ratio threshold, the processing device 140A may determine that the first detection result satisfies the condition. As another example, in response to determining that the third ratio is equal to the third ratio threshold, the processing device 140A may determine that the first detection result fails to satisfy the condition.

In some embodiments, the processing device 140A may determine whether the second detection result satisfies the condition based on the detection result(s). In some embodiments, the processing device 140A may determine whether the second detection result is within the range of the image, e.g., a center region in the image, indicating whether the lung is located at or sufficiently near to the center region of the image. In response to determining that the second detection result is within the range of the image, the processing device 140A may determine the second detection result satisfies the condition. In response to determining that the second detection result is beyond the range of the image, the processing device 140A may determine the second detection result fails to satisfy the condition.

In some embodiments, the range may be set according to default settings of the image processing system 100 or by a user. In some embodiments, the range may be determined based on a plurality of sample images (e.g., 493 sample images). The second detection result of an image may include a box of a shape enclosing one or both lungs of a subject. The box may be of the shape of a polygon, a circle, an ellipse, etc., defined by a boundary or contour. In some embodiments, the range may be defined by one or more distance thresholds between the boundary or contour of the box and one or more edges of the image (or a region within the image). In some embodiments, the range may be defined by one or more distance thresholds between the boundary or contour of the box and a certain point or region in the image (e.g., a center of the image, a center region in the image). Any one of the one or more distance thresholds may be expressed in terms of a value in the length dimension, or a dimensionless value (e.g., a value normalized with respect to a length, e.g., the dimension of an edge of an image or a region within the image).

For instance, the second detection result of an image may include a rectangular box enclosing a lung, and the rectangular box is defined by an upper boundary parallel to an upper edge of the image, a lower boundary parallel to an lower edge of the image, a right boundary parallel to a right edge of the image, and a left boundary parallel to a left edge of the image; the range may be defined by a first distance threshold between the upper boundary of the rectangular box to the upper edge of the image, a second distance threshold between the lower boundary of the rectangular box to the lower edge of the image, a third distance threshold between the right boundary of the rectangular box to the right edge of the image, and a fourth distance threshold between the left boundary of the rectangular box to the left edge of the image.

In some embodiments, the range may be set according to default settings of the image processing system 100 or by a user. In some embodiments, the range may be determined offline by the processing device 140A, the processing device 140B, or a processing device other than the processing device 140A and the processing device 140B. Merely by way of example, the following descriptions are provided in which the processing device 140B is configured to determine the range.

In some embodiments, the processing device 140B may determine the range by determining each of the one or more distance thresholds according to the process the same as or similar to the process for determining the ratio threshold as already described. For instance, for each of sample images (e.g., 443 sample images) that meets an imaging standard with respect to the overlapping region between the scapula and the lung in the sample image, the processing device 140B may determine one or more of a first sample distance, a second sample distance, a third sample distance, and a fourth sample distance between a certain sample point or sample region or the boundary or contour of the box of the lung and an upper edge of the sample image (or a region within the sample image), a lower edge of the sample image (or the region within the sample image), a right edge of the sample image (or the region within the sample image), and a left edge of the sample image (or the region within the sample image), respectively. The processing device 140B may determine the one or more of the first distance threshold, the second distance threshold, the third distance threshold, and the fourth distance threshold based on the sample distances. In some embodiments, the processing device 140 may also normalize the sample distances, and determine the range based on thereof. For example, the processing device 140B may designate the range or a middle part of the range of the first sample (and normalized) distances, the range or a middle part of the range of the second sample (and normalized) distances, a range or a middle part of the range of the third sample (and normalized) distances and a range or a middle part of the range of the fourth sample (and normalized) distances as the first distance threshold, the second distance threshold, the third distance threshold, and the fourth distance threshold, respectively. For example, the first distance threshold and the second distance threshold may be a first value in the range of 0.031-0.062, respectively. The third distance threshold and the fourth distance threshold may be a second value in the range of 0.012-0.035, respectively. The first value and/or the second value may be set according to default settings of the image processing system 100 or by a user. In some embodiments, similar to the process for determining the ratio threshold as already described, the processing device 140 may set the first value and/or the second value based on one or more accuracy rates determined based on one or more values within the range of 0.031-0.062 and 0.012-0.035 and the sample images. For example, the processing device 140 may designate a value within the range of 0.031-0.062 corresponding to the maximum accuracy rate as the first distance threshold and the second distance threshold and a value within the range of 0.012-0.035 corresponding to the maximum accuracy rate as the third distance threshold and the fourth distance threshold.

In some embodiments, the processing device 140A may determine whether the third detection result satisfies the condition based on the detection result(s). In some embodiments, the processing device 140A may determine whether the confidence value of the third detection result is smaller than the confidence value threshold, indicating whether the image includes a foreign object. In response to determining that the confidence value of the third detection result is smaller than the confidence value threshold, the processing device 140A may determine the third detection result satisfies the condition. In response to determining that the confidence value of the third detection result exceeds the confidence value threshold (e.g., 0.2-0.8), the processing device 140A may determine the third detection result fails to satisfy the condition. In some embodiments, the confidence value threshold may be set according to default settings of the image processing system 100 or by a user. It should be noted that, in response to determining that the confidence value of the third detection result is equal to the confidence value threshold, the processing device 140A may determine that the third detection result satisfies the condition or not. For example, in response to determining that the confidence value of the third detection result is equal to the confidence value threshold, the processing device 140A may determine that the third detection result satisfies the condition. As another example, in response to determining that the confidence value of the third detection result is equal to the confidence value threshold, the processing device 140A may determine that the third detection result fails to satisfy the condition.

In some embodiments, the processing device 140A may determine whether the fourth detection satisfies the condition based on the detection result(s). In some embodiments, the processing device 140A may determine whether the offset value of the fourth detection result relative to the reference line is smaller than an offset threshold, indicating whether the spine is located at or sufficiently near to the center of the image. For example, the reference line may include a centerline of the image. In response to determining that the offset value of the fourth detection result to the reference line is smaller than the offset threshold, the processing device 140A may determine the fourth detection result satisfies the condition. In response to determining that the offset value of the fourth detection result to the reference line exceeds the offset threshold, the processing device 140A may determine the fourth detection result fails to satisfy the condition. It should be noted that, in response to determining that the offset value of the fourth detection result to the reference line is equal to the offset threshold, the processing device 140A may determine that the fourth detection result satisfies the condition or not. For example, in response to determining that the offset value of the fourth detection result to the reference line is equal to the offset threshold, the processing device 140A may determine that the fourth detection result satisfies the condition. As another example, in response to determining that the offset value of the fourth detection result to the reference line is equal to the offset threshold, the processing device 140A may determine that the fourth detection result fails to satisfy the condition.

In some embodiments, the offset threshold may be set according to default settings of the image processing system 100 or by a user. In some embodiments, the offset threshold may be determined offline by the processing device 140A, the processing device 140B or a processing device other than the processing device 140A and the processing device 140B. Merely by way of example, the following descriptions are provided in which the processing device 140B is configured to determine the offset threshold.

In some embodiments, the processing device 140B may determine the offset threshold based on a plurality of sample images. In some embodiments, the processing device 140B may determine the range based on the sample images according to the process the same as or similar to the process for determining the ratio threshold as already described. For illustration purposes, the plurality of sample images may have been analyzed and labeled as satisfying the imaging standard with respect to the spine or not. The prior analysis and labeling may be performed by, e.g., one or more users, one or more processing devices (e.g., based on the detection model), etc. The prior labeling of a sample image may be referred to as an actual determination result of the sample image. For each sample image, the processing device 140B may determine a relative value of a total of distances between one or more points of a sample spine and the center point of each sample image. Any one of the total distances may be expressed in terms of a value in the length dimension, or a dimensionless value (e.g., a value normalized with respect to a length). In some embodiments, the processing device 140B may determine the relative value by normalizing the total distances of each sample image. The processing device 140B may determine the offset threshold based on the relative values. In some embodiments, the processing device 140B may set a candidate threshold. The processing device 140B may generate a determination result of each of the sample image based on the candidate threshold and the relative values. If an absolute value of a relative value of a sample image exceeds the candidate threshold, the processing device 140B may deem that the sample spine in the sample image fails to meet an imaging standard with respect to the spine. If the absolute value of the relative value of a sample image is smaller than the candidate threshold, the processing device 140B may deem that the sample spine in the sample image meets the imaging standard with respect to the spine. The processing device 140B may determine an accuracy rate associated with the determination results by comparing the determination results with the actual determination results. For illustration purposes, if a determination result of a sample image is consistent with an actual determination result of the sample image, the processing device 140B may determine that the determination result of the sample image is accurate. If the determination result of the sample image is different from the actual determination result of the sample image, the processing device 140B may determine that the determination result of the sample image is inaccurate. If the accuracy rate associated with the determination results is smaller than the preset value, the processing device 140B may designate the candidate offset threshold as the offset threshold. If the accuracy rate associated with the determination results is smaller than the preset value, the processing device 140B may adjust the candidate ratio threshold and repeat the process for determining the offset threshold based on the candidate ratio threshold as already described. For example, among 490 sample images available for determining the offset threshold, based on a candidate offset threshold (e.g., a candidate offset threshold of 0.02-0.07), 400 sample images meet the imaging standard with respect to the spine, and 90 sample images fails to meet the imaging standard, and the accuracy rate associated with the determination results exceeds 95%, the processing device 140B may designate a value in the range of 0.02-0.07 as the offset threshold. The value may be set according to default settings of the image processing system 100 or by a user.

In 630, the processing device 140A (e.g., the image metric generation module 420) may generate the image metric of the image based on the determination result. As described in connection with operation 520, the quality of the image may be characterized by the image quality classification of the image. The image quality classification may indicate the confidence level for generating the clinical finding using the image. The image quality classification may include the first level and the second level. Additionally or alternatively, the image quality classification may include the first level, the intermediate level, and the second level. In some embodiments, if the image belongs to the first level, the image can be used to generate a clinical finding. If the image belongs to the intermediate level, the image can be used to generate a clinical finding. If the image belongs to the second level, the image may not be used to generate a clinical finding.

In some embodiments, the processing device 140A may determine that the image belongs to the first level. For instance, in response to determining that the detection result(s) satisfies the condition, the processing device 140A may determine that the image belongs to the first level.

In some embodiments, the processing device 140A may determine that the image belongs to the second level. For instance, in response to determining that the detection result(s) fails to satisfy the condition, the processing device 140A may determine that the image belongs to the second level. In response to determining that the second detection result fails to satisfy the condition, the processing device 140A may determine that the image belongs to the second level.

In some embodiments, the processing device 140A may determine that the image belongs to the intermediate level. For example, in response to determining that the second detection result and the third detection result satisfy the condition, and that at least one of the fourth detection result or the first detection result fails to satisfy the condition, the processing device 140A may determine that the image belongs to the intermediate level. As another example, in response to determining that the second detection result satisfies the condition, and that at least one of the fourth detection result or the first detection result fails to satisfy the condition, the processing device 140A may determine that the image belongs to the intermediate level.

Merely by way of example, in response to determining a first item that the first detection result, the second detection result, and the fourth detection result satisfy the condition, a second item that the third detection result fails to satisfy the condition, and a third item that the third detection result is located outside the second detection result (one or more of the three items being satisfied), the processing device 140A may determine that the image belongs to the intermediate level.

Merely by way of example, in response to determining a first item that the first detection result, the second detection result, and the fourth detection result satisfy the condition, a second item that the third detection result fails to satisfy the condition, and a third item that the third detection result is inside the second detection result (one or more of the three items being satisfied), the processing device 140A may determine that the image belongs to the second level.

For illustration purposes, the detection result(s) may include the second detection result and the third detection result. In response to determining a first item that the second detection result satisfies the condition, a second item that the third detection result fails to satisfy the condition, and a third item that the third detection result is located outside the second detection result (one or more of the three items being satisfied), the processing device 140A may determine that the image belongs to the intermediate level. In response to determining a first item that the second detection result satisfies the condition, a second item that the third detection result fails to satisfy the condition, and a third item that the third detection result is located inside the second detection result (one or more of the three items being satisfied), the processing device 140A may determine that the image belongs to the second level.

In some embodiments, the processing device 140A may allocate different weights to the different detection results. For example, the second detection result may have a higher weight than both the first detection result and the fourth detection result. Accordingly, if the second detection result fails to satisfy the condition, the image may be designated as belonging to the second level. However, if the second detection result satisfies the condition, and one of the first detection result or the fourth detection result fails to satisfy the condition, the image may be designated as belonging to the intermediate level. If the second detection result satisfies the condition, and the first detection result and the fourth detection result both fail to satisfy the condition, the image may be designated as belonging to the second level. In some embodiments, the clinical finding may include at least one pathological condition of the object(s). In some embodiments, the processing device 140A may allocate different weights (or weighting factors) to the different detection results based on the pathological condition(s). For instance, whether the second detection result corresponding to the lung is satisfactory may affect the accuracy of the diagnosis of pathological condition(s) relating to one or both lungs. If the second detection result is unsatisfactory, the diagnosis of pathological condition(s) (e.g., pneumothorax) relating to one or both lungs may be inaccurate. Thus, the processing device 140A may allocate a relatively high weight to the second detection result.

In some embodiments, the processing device 140A may generate an explanation why the image belongs to the intermediate level or the second level. In some embodiments, the explanation may include at least one of the parameter(s) that fails to satisfy the condition, the name of an object whose detection result fails to satisfy the condition, or the like, or a combination thereof. For example, if the first ratio fails to satisfy the condition, the explanation may include the first ratio and/or the scapula.

It should be noted the descriptions presented above are intended to be illustrative. In some embodiments, the processing device 140A may process the image using the detection model to directly generate the image quality classification together with the detection result(s).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more other optional operation (e.g., a storage operation) may be added in the process 600. In the storage operation, the processing device 140A may store the image metric of the image in the storage device (e.g., the storage device 150). In some embodiments, the image metric may be transmitted to or stored in a picture archiving and communication system (PACS), thereby implementing functions including, e.g., intelligently pre-screening the disease in the image, aiding in reviewing the image and/or generating the clinical finding, re-reading the image metric, etc.

Figure 7:
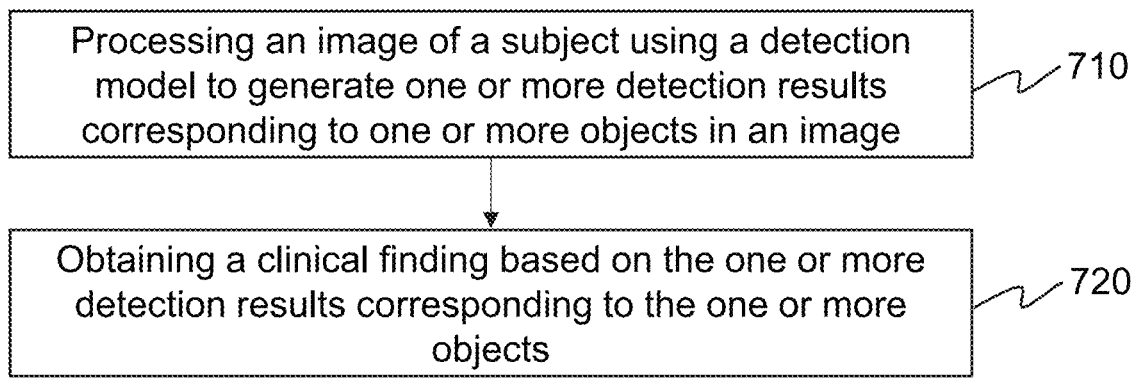
FIG. 7 is a flowchart illustrating an exemplary process for generating a clinical finding based on a detection model according to some embodiments of the present disclosure.

FIG. 7 is a flowchart illustrating an exemplary process for generating a clinical finding based on a detection model according to some embodiments of the present disclosure. In some embodiments, the process 700 may be implemented in the image processing system 100 illustrated in FIG. 1. For example, the process 700 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140A illustrated in FIG. 4A). The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 140A (e.g., the image processing module 410) may process an image of a subject using a detection model to generate one or more detection results corresponding to one or more objects in an image. In some embodiments, the processing device 140A may obtain the image from a component (e.g., the imaging device 110, the terminal 130, the storage device 150) of the imaging processing system 100. For example, the image may be acquired by the imaging device 110. The processing device 140A may obtain the image directly from the imaging device 110, or from a storage device (e.g., the storage device 150) where an image acquired by the imaging device 110 (or another imaging device) in advance is stored. In some embodiments, the processing device 140A may obtain the image from a source external to the image processing system 100.

As illustrated in connection with operation 510 or 610, the image may include a chest image of the subject. For illustration purposes, the image may include an image of a frontal chest of the subject. Exemplary objects in the image may include a lung, a spine, a scapula, a heart, a foreign object, an abnormal part, or a portion thereof, in the image. Exemplary detection result(s) may include a detection result corresponding to a scapula, a detection result corresponding to a lung, a detection result corresponding to a foreign object, a detection result corresponding to a spine, a detection result corresponding to a heart, a detection result corresponding to an abnormal part, or the like, or any combination thereof. For example, a detection result corresponding to an object may include a position of the object, a bounding box of the object, a contour of the object, a region of the object, a dimension of the object, or the like, or any combination thereof.

In some embodiments, the processing device 140A may preprocess the image, and generate the detection result(s) based on the preprocessed image using the detection model. For example, the processing device 140A may input the preprocessed image into the detection model and generate the detection result(s). More descriptions of preprocessing the image may be found elsewhere in the present disclosure. See, e.g., operation 510 or 610 and the descriptions thereof.

In 720, the processing device 140A (e.g., the image metric generation module 420) may generate a clinical finding based on the one or more detection results corresponding to the one or more objects. As illustrated in connection with 520, the clinical finding may indicate the physiological condition of the object(s) in the image. For example, the physiological condition may include the normal (or healthy) condition and the abnormal (unhealthy or pathological) condition of the object. For illustration purposes, the clinical finding may include at least one parameter of the object(s), at least one pathological condition of the object(s), a severity degree of a pathological condition, or the like, or any combination thereof. Taking a chest image as an example, the parameter(s) may include the width of the heart, the width of the lung, a ratio between the width of the heart to the width of the lung, a ratio of a volume of the abnormal part to a volume of the lung, or the like, or any combination thereof. Exemplary pathological conditions may include cardiac hypertrophy, pneumothorax, pleural effusion, pneumonia, tumor, or the like, or any combination thereof.

Figure 13A:
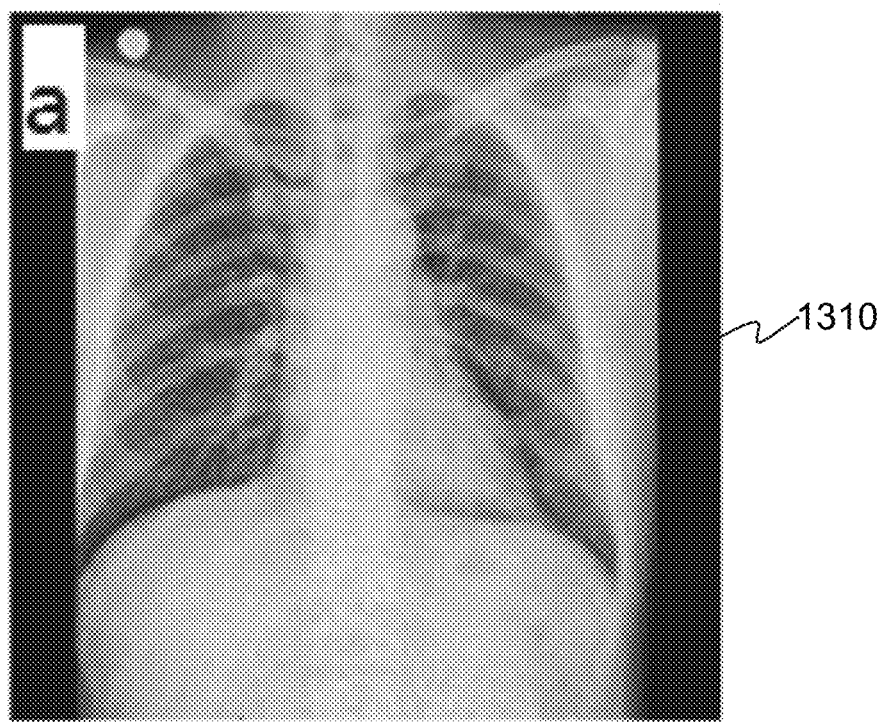
FIGS. 13a-16b illustrate exemplary detection results corresponding to one or more objects in an image determined based on a detection model according to some embodiments of the present disclosure.

In some embodiments, the processing device 140A may determine a fourth ratio of the width of the fifth detection result to the second detection result based on the fifth detection result and the second detection result. The processing device 140A may determine the width of the fifth detection result based on the fifth detection result. The processing device 140A may determine the width of the second detection result based on the second detection result. In some embodiments, the width of the fifth detection result may include the maximum width of the fifth detection result. The width of the second detection result may include the maximum width of the second detection result. The fourth ratio may include a ratio of the maximum width of the fifth detection result to the maximum width of the second detection result. For example, the processing device 140A may determine a first line (e.g., line 1340 as illustrated in FIG. 13) passing a leftmost point and a second line (e.g., line 1330 as illustrated in FIG. 13) passing the rightmost point of the second detection result. The processing device 140A may designate the distance between the first line and the second line as the maximum width of the second detection result. In some embodiments, a process for determining the maximum width of the fifth detection result may be the same as or similar to the process for determining the maximum width of the second detection result. The distance between the first line and the second line may be expressed in terms of a value in the length dimension, or a dimensionless value (e.g., a value normalized with respect to a length).

In practice, if a ratio between the width of the heart to the width of the lung exceeds a fourth ratio threshold (e.g., 50%), the subject (e.g., a patient) may have a pathological condition of cardiac hypertrophy. The processing device 140A may compare the fourth ratio with the fourth ratio threshold to determine whether the pathological condition of cardiac hypertrophy exists. In response to determining that the fourth ratio exceeds the fourth ratio threshold, the processing device 140A may determine the clinical finding that the pathological condition of cardiac hypertrophy exists. In some embodiments, the clinical finding may also include the fourth ratio. In some embodiments, the processing device 140A may generate a notification including the fourth ratio and the pathological condition of cardiac hypertrophy.

In response to determining that the fourth ratio is smaller than the fourth ratio threshold, the processing device 140A may determine the pathological condition of cardiac hypertrophy is absent, and the clinical finding may include the fourth ratio. In some embodiments, the processing device 140A may generate a notification including the fourth ratio. In this case, the detection model may be configured to determine the fifth detection result and the second detection result. For example, the detection model may include a single model configured to determine the fifth detection result and the second detection result. As another example, the detection model may include a heart detection sub-model and a lung detection sub-model configured to determine the fifth detection result and the second detection result, respectively.

In some embodiments, if the object(s) include an abnormal part, the processing device 140A may determine a pathological condition of the abnormal part based on the sixth detection result corresponding to the abnormal part. For example, the pathological condition of the abnormal part may include pneumothorax, pleural effusion, pneumonia, tumor, or the like, or any combination thereof.

If the pathological condition of the abnormal part includes pneumothorax, the processing device 140A may determine that the clinical finding includes the pathological condition of pneumothorax. In some embodiments, the processing device 140A may determine a fifth ratio of a count of elements (e.g., pixels, voles) of the sixth detection result to a count of elements (e.g., pixels, voles) of the second detection result. In response to determining that the fifth ratio exceeds a fifth ratio threshold (e.g., 40%), the processing device 140A may determine that the pathological condition of high-risk pneumothorax exists. In some embodiments, the clinical finding may also include the fifth ratio. In some embodiments, the processing device 140A may generate a notification including the fifth ratio and high-risk pneumothorax. In response to determining that the fifth ratio is smaller than a sixth ratio threshold (e.g., 10%), the processing device 140A may determine that the pathological condition of self-healing pneumothorax exists. In some embodiments, the clinical finding may also include the fifth ratio. In some embodiments, the processing device 140A may generate a notification including the fifth ratio and self-healing pneumothorax.

If the pathological condition of the abnormal part includes pleural effusion, the processing device 140A may determine that the clinical finding includes the pathological condition of pleural effusion. In some embodiments, the processing device 140A may determine a sixth ratio of a count of elements (e.g., pixels, voles) of the sixth detection result to a count of elements (e.g., pixels, voles) of the second detection result. In response to determining that the sixth ratio exceeds a seventh ratio threshold (e.g., 40%), the processing device 140A may determine that a pathological condition of high-risk pleural effusion exists. In some embodiments, the clinical finding may also include the sixth ratio. In some embodiments, the processing device 140A may generate a notification including the sixth ratio and high-risk pleural effusion.

In response to determining that the sixth ratio is smaller than an eighth ratio threshold (e.g., 10%), the processing device 140A may determine that a pathological condition of self-healing pleural effusion exists. In some embodiments, the clinical finding may also include the sixth ratio. In some embodiments, the processing device 140A may generate a notification including the sixth ratio and self-healing pleural effusion. In this case, the detection model may be configured to determine the sixth detection result and the second detection result. For example, the detection model may include a single model configured to determine the sixth detection result and the second detection result. In some embodiments, the detection model may include an abnormal part detection sub-model and a lung detection sub-model configured to determine the sixth detection result and the second detection result, respectively.

In some embodiments, the detection model may include multiple detection sub-models, and each detection sub-model may be configured to determine a detection result associated with one type of the pathological condition of the abnormal part. For example, the detection model may include a pneumothorax detection sub-model, a pleural effusion detection sub-model, a pneumonia detection sub-model, or a tumor detection sub-model. The pneumothorax detection sub-model may be configured to determine a detection result corresponding to an abnormal part caused by pneumothorax. The pleural effusion detection sub-model may be configured to determine a detection result corresponding to an abnormal part caused by pleural effusion. The pneumonia detection sub-model may be configured to determine a detection result corresponding to an abnormal part caused by pneumonia. The tumor detection sub-model may be configured to determine a detection result corresponding to an abnormal part caused by tumor.

It should be noted the descriptions presented above are intended to be illustrative. In some embodiments, the processing device 140A may process the image of the subject using the detection model to generate at least a part of the clinical finding together with the detection result(s). For example, the processing device 140A may process the image of the subject using the detection model to generate the parameter(s) together with the detection result(s). The pathological condition may be determined by a doctor. As another example, the processing device 140A may process the image of the subject using the detection model to generate the parameter(s) and the pathological condition(s) together with the detection result(s). Moreover, if another different part of a subject (e.g., brain, a limb) or one or more different objects (e.g., the prostate, the ovary, the uterus, the kidney, the stomach, the pancreases) are of interest, applicable clinical conditions may be applied in the assessment of image quality and/or determination of a relevant clinical finding.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, before operation 720, the processing device 140A may determine an image quality classification of the image. If the image belongs to the first level or the intermediate level as illustrated in FIGS. 5-6, the processing device 140A may implement operation 720. If the image belongs to the second level, the processing device 140A may omit operation 720.

Figure 8:
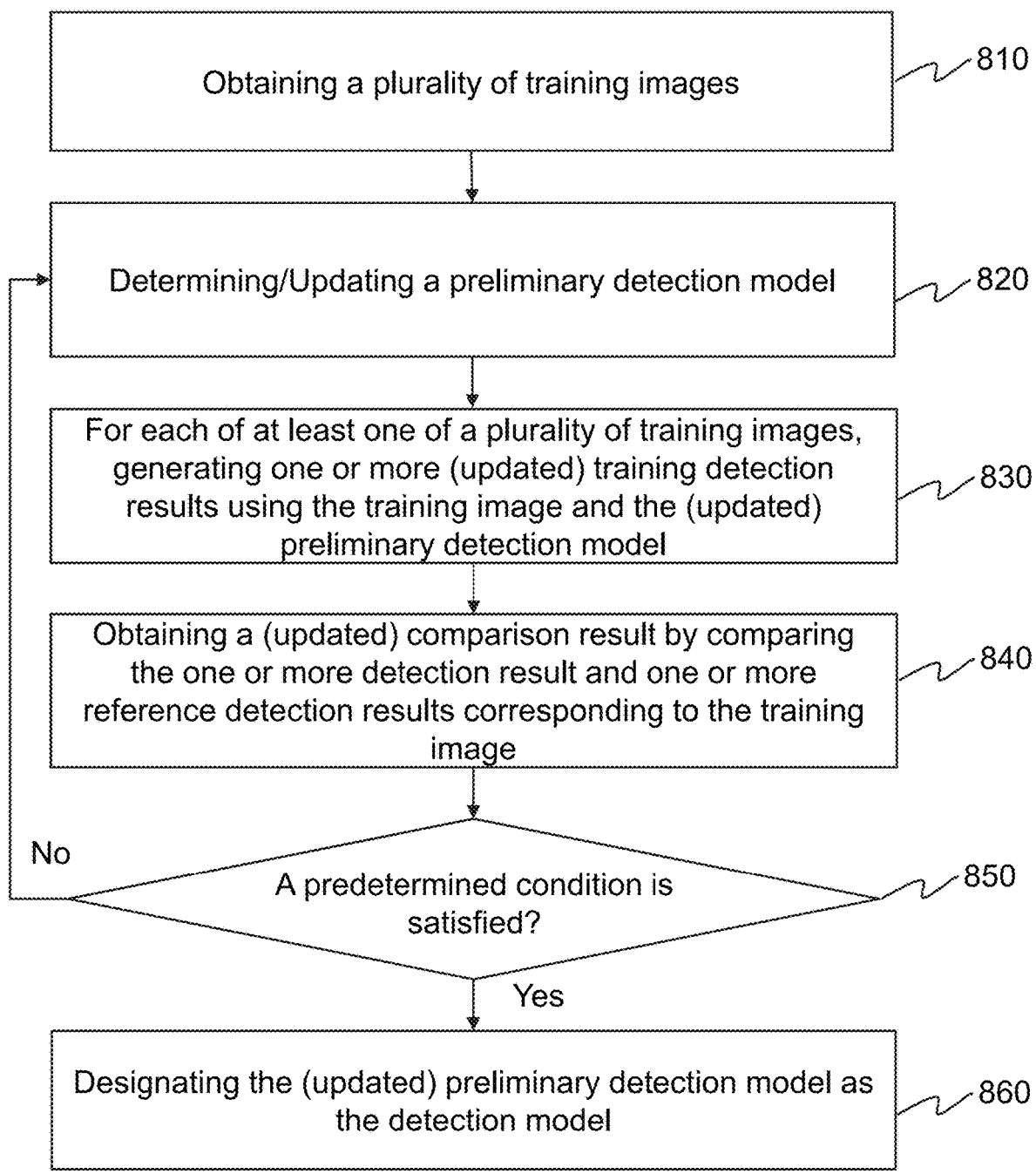
FIG. 8 is a flowchart illustrating an exemplary process for generating a detection model according to some embodiments of the present disclosure.

FIG. 8 is a flowchart illustrating an exemplary process for generating a detection model according to some embodiments of the present disclosure. In some embodiments, the process 800 may be implemented in the image processing system 100 illustrated in FIG. 1. For example, the process 800 may be stored in a storage medium (e.g., the storage device 150, or the storage 220 of the processing device 140) as a form of instructions, and can be invoked and/or executed by the processing device 140 (e.g., the processor 210 of the processing device 140, or one or more modules in the processing device 140B illustrated in FIG. 4B). The operations of the illustrated process 800 presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the detection model as illustrated in FIGS. 5-7 may be trained based on the process 800.

In 810, the processing device 140B (e.g., the model training module 430) may obtain a plurality of training images. Similar to the image as illustrated in FIGS. 5-7, the training image may include a two-dimensional (2D) image, a three-dimensional (3D) image, a four-dimensional (4D) image, etc. As another example, the training image may include a magnetic resonance (MR) image (e.g., a streaming MR image, a volumetric MR image, a cine MR image), a computed tomography (CT) image (e.g., a cone-beam CT (CBCT) image), a positron emission tomography (PET) image (e.g., a single-photon emission computed tomography (SPECT) image), a functional MR image (e.g., an fMR image, a dynamic contrast-enhanced MR (DCE-MR) image, a diffusion MR image), a fluoroscopic image, an ultrasound image, a radiotherapy portal image, or the like, or any combination thereof.

In some embodiments, the training images may include one or more training chest images. Similar to the chest image as illustrated in FIG. 5, a training chest image may include a representation of the interior of the chest of a subject (e.g., a patient). In some embodiments, the training images may include one or more training images of frontal chests. Exemplary training object(s) in the training image may include a lung, a spine, a scapula, a heart, a foreign object, a heart, an abnormal part, or a portion thereof, or the like, or any combination thereof.

In some embodiments, the processing device 140B may obtain the training images from a storage device (e.g., the storage device 150, the storage 220, the storage 390) disclosed elsewhere in the present disclosure or a third party (e.g., an external device). In some embodiments, the processing device 140B may obtain a plurality of first images from the storage device. The processing device 140B may obtain a plurality of second images by transforming some of the first images. The training images may include at least some of the first images and at least some of the second images. For example, the training images may include the first images and the second images. As another example, the training images may include a part of the first images and the second images. By doing this, the count or number of the training images may significantly increase, e.g., to exceed a threshold, without actually collect new images. In some embodiments, the count or number of the training images may affect the accuracy of a detection model generated based on the training images. For example, if the count or number of the training images exceeds the threshold, the accuracy of the detection model so trained may be deemed sufficient. Besides, the volume and/or diversity of the training images may increase and the applicability and robustness of the detection model may be improved.

In some embodiments, the processing device 140B may transform a first image by adjusting a size of a first training object in the first image, rotating a second training object in the first image, filling a third training object in the first image, translating a fourth training object in the first image, flipping the first image, cropping the first image, adjusting a contrast ratio of the first image, or the like, or any combination thereof. For example, the processing device 140B may transform a first image by rotating a training object by 90 degrees. As another example, the processing device 140B may transform a first image by rotating a training object by 180 degrees. In some embodiments, at least two of the first training object, the second training object, the third training object, or the fourth training object may be the same training object, e.g., the lung. In some embodiments, the first training object, the second training object, the third training object, or the fourth training object may be different.

In 820, the processing device 140B (e.g., the model training module 430) may obtain a preliminary detection model. In some embodiments, the preliminary detection model may include a deep learning model, e.g., a convolutional neural network model, a support vector machine (SVM) model, etc. For example, the preliminary detection model may include a volumetric network (V-net) model, a LinkNet model, a fully convolutional DenseNet (FC-DenseNet) model, a faster region-based convolutional neural network (Faster-RCNN) model, a RetinaNet model, a you-only-look-once (YOLO) network model, a region-based convolutional neural network (RCNN) model, a single shot multibox (SSD) model, a single-shot refinement neural network (RefineDet) model, or the like, or any combination thereof.

In some embodiments, the preliminary detection model may include a plurality of layers, e.g., an input layer, one or more hidden layers, an output layer, or the like, or any combination thereof. For illustration purposes, the one or more hidden layer may be configured to perform specific functions, e.g., convolution, pooling, normalization, matrix multiplication, non-linear activation, or the like, or any combination thereof. In some embodiments, each of at least a portion (e.g., a convolutional layer) of the plurality of layers may include a plurality of kernels configured to extract a feature representation of one or more training detection result(s) corresponding to one or more training objects of a training image. In some embodiments, the preliminary detection model may include a plurality of neurons configured to establish connection (e.g., connection between a pooling layer and a fully connected layer) between at least a portion of the plurality of layers. In some embodiments, the preliminary detection model may include at least one skip-connection structure. The at least one skip-connection structure may allow an additional feature representation of the training detection result(s) to be transmitted from a first layer to a second layer of the plurality of layers.

In some embodiments, the preliminary detection model may include a plurality of parameters (also referred to as "training parameters"). For example, the training parameters may include the size of a kernel of a layer, the total count (or number) of layers, the count (or number) of nodes in a layer, a learning rate, a batch size, an epoch, a connected weight between two connected nodes, a bias vector relating to a node, an activation vector of a node in a layer, or the like, or any combination thereof. In some embodiments, the processing device 140B may initialize or set the training parameters. For example, the processing device 140B may set a connected weight to be a random value in a range from −1 to 1. As another example, the processing device 140*b* may set a bias vector to be a random value in a range from 0 to 1. In some embodiments, the processing device 140*b* may initialize or set the parameters based on a Gaussian random algorithm, a Xavier algorithm, etc.

In 830, for each of at least one of the plurality of training images (also referred to as "first training images"), the processing device 140*b* (e.g., the model training module 430) may generate one or more training detection results using the training image and the preliminary detection model. The process for generating the training detection result(s) may be similar to the process for generating the detection result(s) as illustrated in FIGS. 5-7. In some embodiments, the processing device 140B may input the training image into the preliminary detection model and the training detection result may be output by the preliminary detection model.

In some embodiments, the processing device 140B may preprocess the training image. The processing device 140B may input the processed training image into the preliminary detection model, and the training detection result may be output by the preliminary detection model. In some embodiments, the processing device 140B may preprocess the training image by normalizing the training image, adjusting the size of the training image, rotating the training image, flipping the image, cropping the image, changing a contrast ratio of the training image, removing artifact and/or noise of the training image, or the like, or a combination thereof.

Figure 9A:
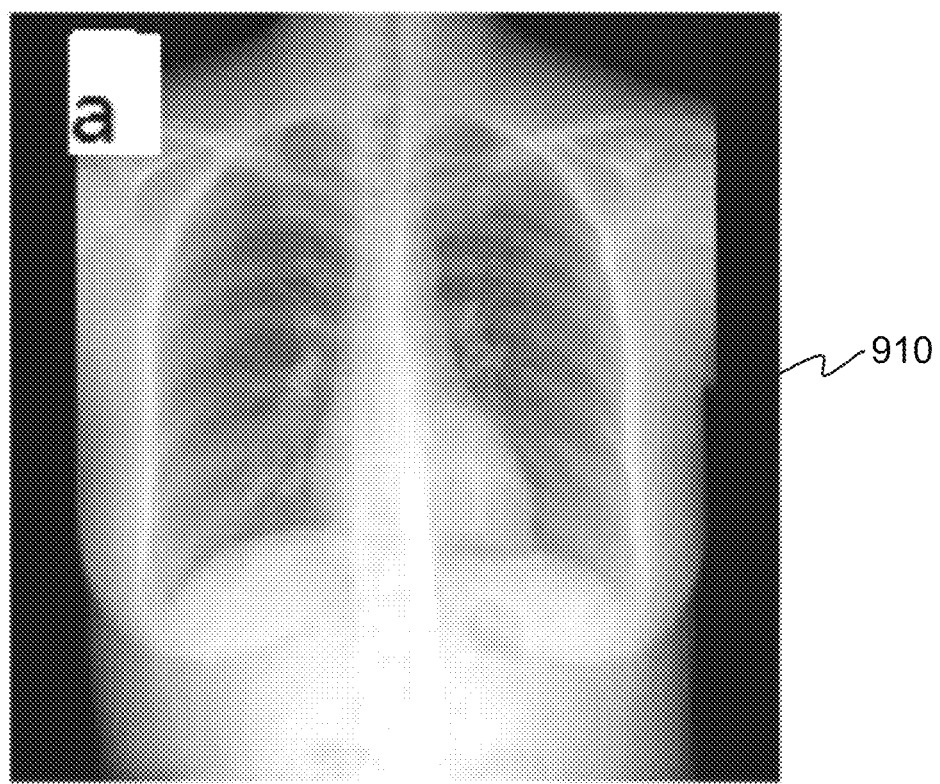
FIGS. 9a-12b illustrate exemplary reference detection results corresponding to one or more objects in an image according to some embodiments of the present disclosure.
Figure 9B:
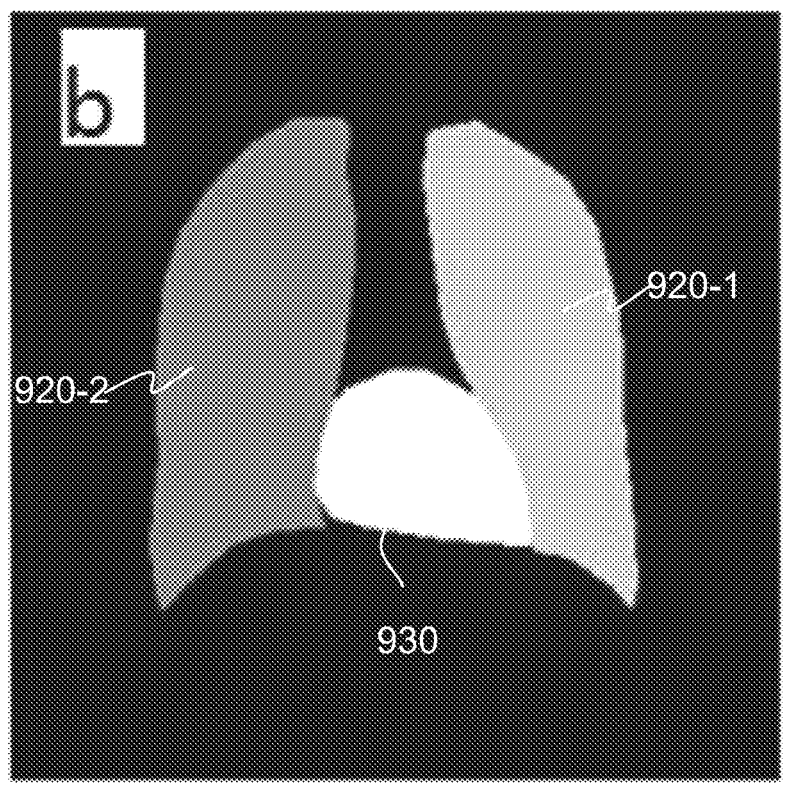
Figure 10A:
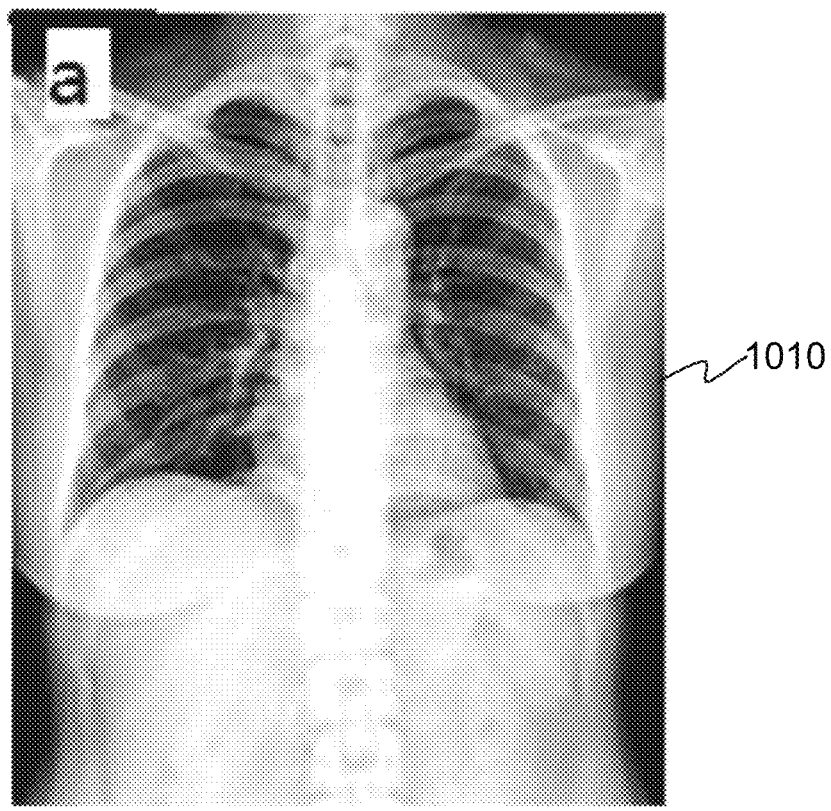
Figure 10B:
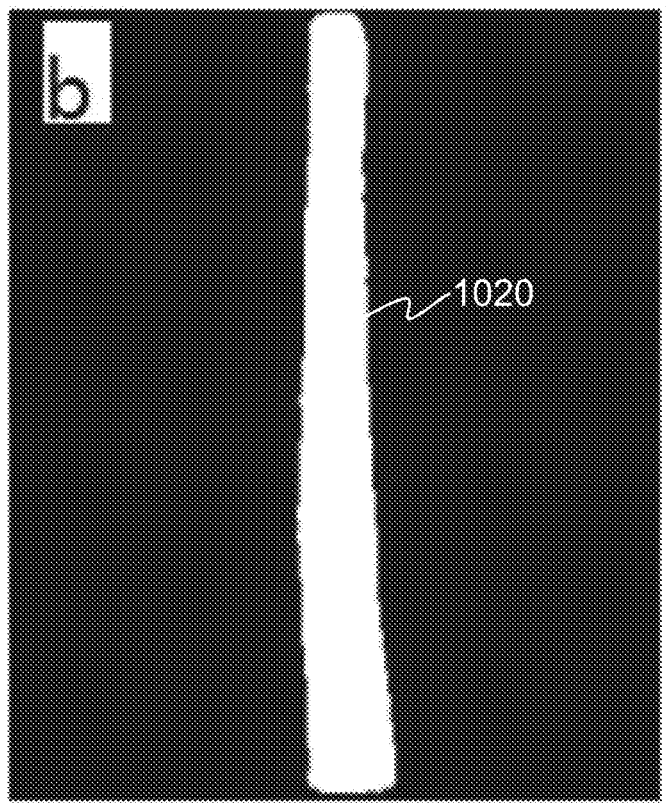
Figure 11A:
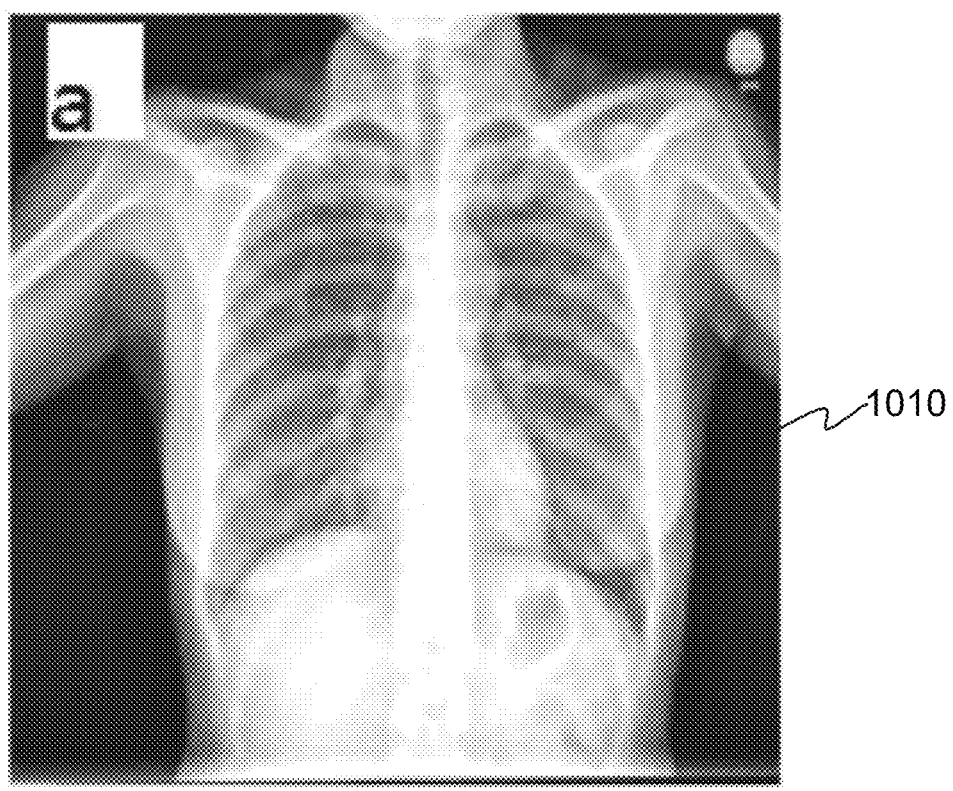
Figure 11B:
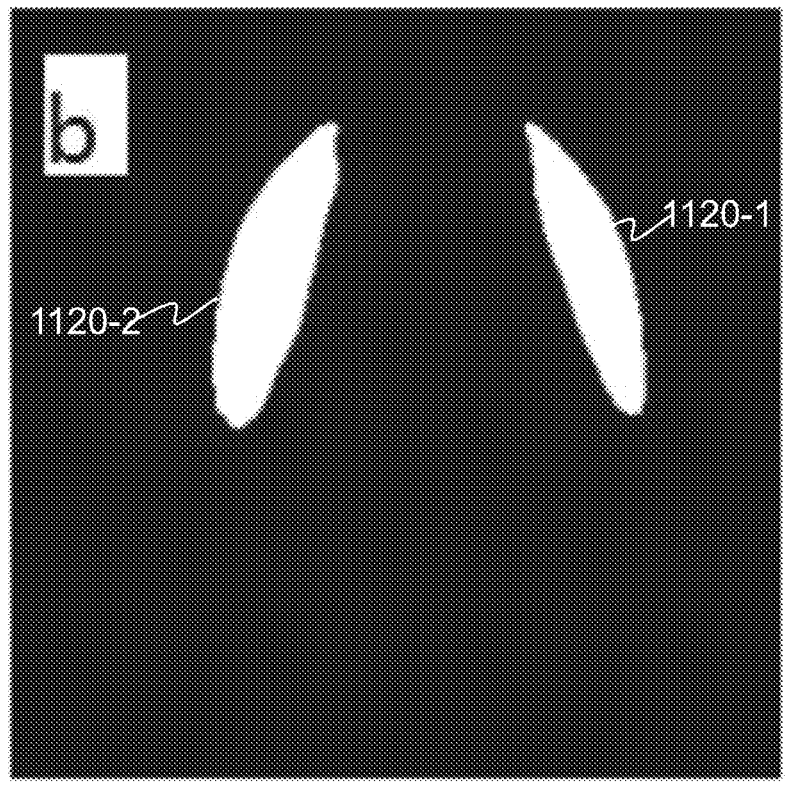
Figure 12A:
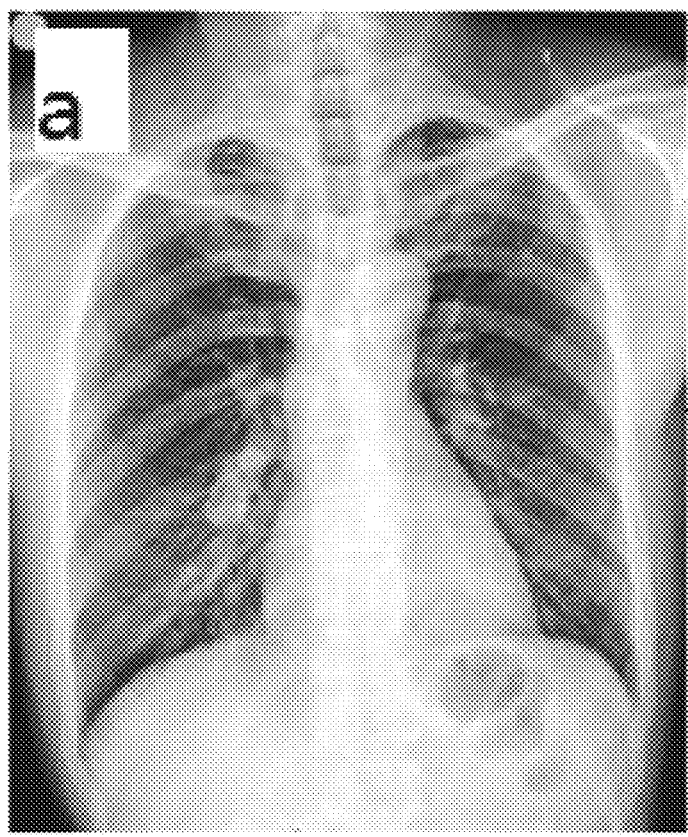
Figure 12B:
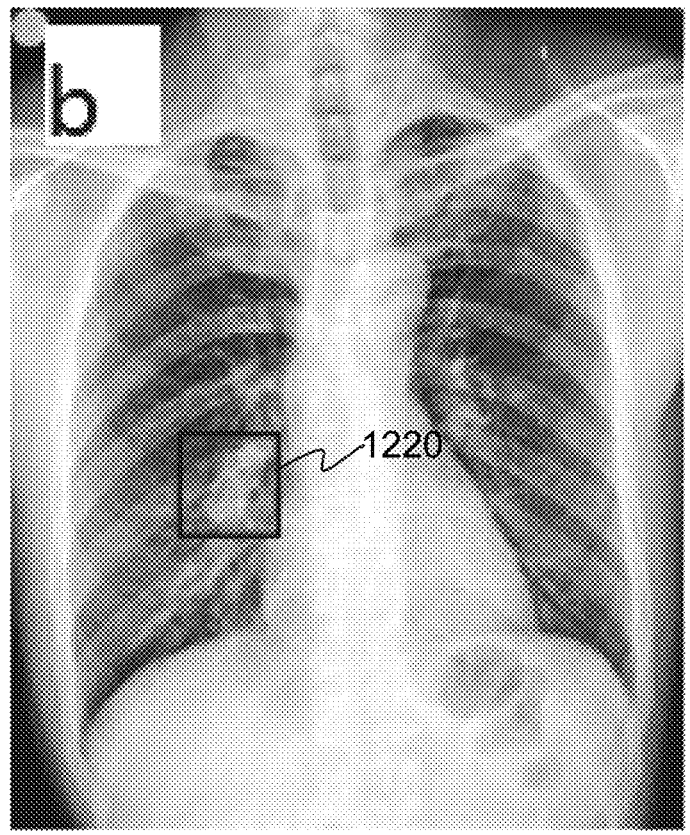

In 840, the processing device 140B (e.g., the model training module 430) may obtain a comparison result by comparing the training detection result(s) and one or more reference detection results corresponding to each first training image. The reference detection result(s) may be a desired output of the preliminary detection model corresponding to the first training image. The reference detection result(s) may also be referred to as one or more masks or ground truths corresponding to one or more training objects in the first training image. Taking a training chest image as an example, the reference detection result(s) may include a first reference detection result (e.g., a region 1120-1 and a region 1120-2 as shown in FIG. 11*b*) corresponding to a scapula, a second reference detection result (e.g., a region 920-1 and a region 920-2 as shown in FIG. 9*b*) corresponding to a lung, a third reference detection result (e.g., a region 1220 as shown in FIG. 12*b*) corresponding to a foreign object, a fourth reference detection result (e.g., a region 1020 as shown in FIG. 10*b*) corresponding to a spine, a fifth reference detection result (e.g., a region 930 as shown in FIG. 9*b*) corresponding to a heart, a sixth reference detection result corresponding to an abnormal part, or the like, or any combination thereof. For example, a reference detection result of a training object may include a position of the training object, a bounding box of the training object, a contour of the training object, a region of the training object, a dimension of the training object, or the like, or any combination thereof.

For example, for each first training image, a reference detection result corresponding to a heart and a reference detection result corresponding to a lung may be determined. As another example, for each first training image, a reference result corresponding to a lung and a reference detection result corresponding to an abnormal part may be determined. As a further example, for each first training image, at least one of a reference result corresponding to a lung, a reference result corresponding to a scapula, a reference result corresponding to a spine, or a reference result corresponding to a foreign object may be determined.

In some embodiments, the reference detection result(s) may be determined by manually or automatically labeling the image. For example, the reference detection result(s) may be determined using an intelligent machine (e.g., a robot) or an algorithm. In some embodiments, the accuracy of the reference detection result(s) may affect the accuracy of detection results determined by the detection model so trained. In some embodiments, the more accurate the reference detection result(s) are, the greater the accuracy of the detection result determined by the detection model may be.

As described in connection with operation 810, the processing device 140B may obtain the training images based on the first images and the second images. The processing device 140B may obtain the second images by transforming some of the first images. In some embodiments, first reference detection results corresponding to the first images may be determined as illustrated below. At least a portion of second reference detection results corresponding to the second images may be determined by transforming the first reference detection results in the same manner as transforming corresponding first mages. For illustration purposes, the processing device 140B may obtain a second image by flipping a first image. If a first image is in a transverse plane, and a corresponding second image is obtained by horizontally flipping the first image, i.e., rotating the first image by 180 degrees about an axis parallel to the transverse plane, one or more second reference detection results (e.g., bounding boxes of objects, regions of objects, contours of objects in the second image) corresponding to the second image may be obtained by horizontally flipping one or more first reference detection results corresponding to the first image, i.e., rotating the one or more first reference detection results by 180 degrees about the axis parallel to the transverse plane. The sizes of the objects in the second image may be the same as the sizes of the objects in the first image. If a first image is in a sagittal plane, and a corresponding second image is obtained by horizontally flipping the first image, i.e., rotating the first image by 180 degrees about an axis parallel to the sagittal plane, one or more second reference detection results (e.g., bounding boxes of objects, regions of objects, contours of objects in the second image) corresponding to the second image may be obtained by horizontally flipping one or more first reference detection results corresponding to the first image, i.e., rotating the one or more first reference detection results by 180 degrees along the axis parallel with the sagittal plane. The sizes of the objects in the second image may be the same as the sizes of the objects in the first image.

In some embodiments, the comparison result may assess a difference between the training detection result(s) and the reference detection result(s). In some embodiments, the processing device 140B may determine an objective function based on the difference as the comparison result. For example, the objective function may include a loss function of the difference, a Root Mean Square Error (RMSE) function, a Mean Absolute Error (MAE) function, etc.

As illustrated in connection with FIG. 5, the processing device 140B may generate the detection model by performing a plurality of iterations to iteratively update the one or more training parameters of the preliminary detection model. For example, the processing device 140B may update the training parameters based on the objective function using a backpropagation (BP) algorithm. A preliminary detection model with one or more updated training parameters in one iteration of the plurality of iterations may be referred to as an updated or intermediate detection model. In each iteration, the processing device 140B may generate one or more training detection results corresponding to one or more training objects in one training image using the preliminary detection model or the updated preliminary detection model.

In some embodiments, the processing device 140B may determine whether to terminate the training process by determining whether a predetermined condition (or referred to a termination condition) is satisfied in 850. In response to determining that the predetermined condition is satisfied, the processing device 140B may designate the preliminary or updated detection model as the detection model in 860. On the other hand, in response to determining that the predetermined condition is not satisfied, the processing device 140B may further update the preliminary or updated detection model. In some embodiments, the processing device 140B may update the preliminary or updated detection model using at least a part of the at least one of the training images.

In some embodiments, the predetermined condition may relate to the comparison result between the training detection result(s) and the reference detection result(s). In some embodiments, the predetermined condition may be satisfied if the value of the objective function is (locally or globally) minimal or smaller than a threshold (e.g., a constant). In some embodiments, the predetermined condition may be satisfied if the value of the objective function converges. The convergence may be deemed to have occurred if the variation of the values of the objective function in two or more consecutive iterations is smaller than a threshold (e.g., a constant).

In some embodiments, the predetermined condition may include, additionally or alternatively, whether a specified count (or number) of iterations (or rounds of training) have been performed, whether parameters of the preliminary or updated detection model converge within a certain rounds (e.g., three rounds, five rounds) of training, etc. For instance, the predetermined condition may be deemed satisfied when the objective function based on the comparison result is (locally or globally) minimal or smaller than a threshold (e.g., a constant) and at least a certain count or number of iterations (or rounds of training) have been performed. As another example, the predetermined condition may be deemed satisfied either when the objective function based on the comparison result converges or when parameters of the preliminary or updated detection model and parameters of the preliminary or updated detection model converge within a certain rounds (e.g., three rounds, five rounds) of training. In some embodiments, the processing device 1406 may transmit the detection model, to a storage device (e.g., the storage device 150, the storage 220, and the storage 390) for storage.

In some embodiments, the processing device 140B may use at least a part of the training images (also referred to as second training images) to validate the detection model. In some embodiments, the second training images may be different from the first training images as illustrated below. For example, the second training image may include training images other than the first training images. In some embodiments, the processing device 140B may process the second training images using the detection model to generate one or more validating detection results corresponding to one or more training objects in each second training image. The processing device 140B may obtain a validating comparison result by comparing the validating detection result(s) with one or more reference detection results corresponding to each second training image. If the validating comparison result fails to satisfy a predetermined validating condition, the processing device 140B may retrain the detection model until a new validating comparison result satisfies the predetermined condition, and a model so obtained may be the detection model as illustrated in FIGS. 5-7. For example, the processing device 140B may use at least a part of the training images (also referred to as "third training images") to retrain the detection model. In some embodiments, the third training images may be the same as or different from the first training images and/or the second training images. In some embodiments, the process for retraining the detection model using the third training images may be the same as training the preliminary detection model using the first images as illustrated above. As used herein, the predetermined validating condition may include a difference between the validating result(s) and the reference validating result(s) being smaller than a preset validating threshold.

As illustrated, the reference detection result(s) may correspond to the training object(s) in the training image. In some embodiments, the reference detection result(s) may include at least one of the first reference detection result, the second reference detection result, the third detection result, or the fourth detection result. Accordingly, the detection model so trained may be configured to determine at least one of a first detection result corresponding to a scapula, a second detection result corresponding to a lung, a third detection result corresponding to a foreign object, or a fourth detection result corresponding to a spine in an image. In some embodiments, the reference detection result(s) may include the second reference detection result and the fifth reference detection result in an image. Accordingly, the detection model so trained may be configured to determine a second detection result corresponding to a lung and a fifth detection result corresponding to a heart in an image. In some embodiments, the reference detection result(s) may include the second reference detection result and the sixth detection result. Accordingly, the detection model so trained may be configured to determine a second detection result corresponding to a lung and a sixth detection result corresponding to an abnormal part in an image.

In some embodiments, the preliminary detection model may be a single model. In some embodiments, the detection model so trained may be a single model configured to determine one or more detection results each of which corresponds to an object in an image. In some embodiments, the detection model so trained may include multiple detection sub-models, the processing device 140B may generate the detection model by separately training the preliminary detection sub-model. For instance, each individual detection sub-model may be trained based on the preliminary detection sub-model and the training images. The training of the preliminary detection sub-model may terminate when a termination condition is deemed satisfied. For instance, the training of a first preliminary detection sub-model may terminate after a first termination condition is deemed satisfied, while the training of a second preliminary detection sub-model may terminate after a second termination condition is deemed satisfied, in which the first termination condition is different from the second termination condition. The training of different detection sub-models may be performed in parallel or sequentially. Separately or individually trained sub-models may be combined to form the detection model. The training of two different detection sub-models may be independent from each other. In some embodiments, the preliminary detection model multiple preliminary sub-models. The processing device 140B may generate the multiple detection sub-models by training the preliminary sub-models separately. In some embodiments, the process for generating the detection sub-models by training the preliminary sub-models separately may be the same as the process for generating the detection model by training the preliminary model described above.

In some embodiments, the desired output of the preliminary detection model corresponding to the training image may also include a reference image quality classification and/or at least a part of a reference clinical finding of the training image. Similar to the reference detection result(s), the reference image quality classification and/or the clinical finding may be determined by manually or automatically labeling the training image. Similar to the image quality classification and/or the clinical finding as illustrated in FIGS. 5-7, the reference image quality classification may include the first level and the second level. Additionally or alternatively, the reference image quality classification may include the first level, the second level, and the intermediate level. The reference clinical finding may include at least one parameter of the training object(s), at least one reference pathological condition of the training object(s), a reference severity degree of a training pathological condition, or the like, or any combination thereof. Accordingly, a detection model so trained may be configured to determine the detection result(s), an image quality classification, and/or at least a part of a clinical finding of an image.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIGS. 9a-12b illustrate exemplary reference detection results corresponding to one or more objects in an image according to some embodiments of the present disclosure.

As illustrated in connection with FIG. 8, the one or more reference detection result corresponding to one of the one or more training objects in the training image may be the desired output of the preliminary detection model corresponding to the training image. Exemplary reference results may include a first reference detection result corresponding to a scapula, a second reference detection result corresponding to a lung, a third reference detection result corresponding to a foreign object, a fourth reference detection result corresponding to a spine, a fifth reference detection result corresponding to a heart, or the like, or any combination thereof. A region 920-1 and a region 920-2 may represent a second reference detection result corresponding to a lung of an image 910 as shown in FIG. 9b. The second reference detection result relates to a position of the lung, a bounding box of the lung, a contour of the lung, a region of the lung, a dimension of the lung of a subject (e.g., a patient), or the like, or any combination thereof. A region 930 may represent a fifth reference detection result corresponding to a heart of the image 910 as shown in FIG. 9b. The fifth reference detection result relates to a position of the heart, a bounding box of the heart, a contour of the heart, a region of the heart, a dimension of the heart of the subject, or the like, or any combination thereof. A region 1010 may represent a fourth reference detection result corresponding to a spine of an image 1010 as shown in FIG. 10b. The fourth reference detection result relates to a position of the spine, a bounding box of the spine, a contour of the spine, a region of the spine, a dimension of the spine of the subject, or the like, or any combination thereof. A region 1120-1 and a region 1120-2 may represent a first reference detection result corresponding to a scapula of an image 1110 as shown in FIG. 11b. The first reference detection result relates to a position of the scapula, a bounding box of the scapula, a contour of the scapula, a region of the scapula, a dimension of the scapula of the subject, or the like, or any combination thereof. A region 1220 may represent a third reference detection result correspond to a foreign object of an image 1210 as shown in FIG. 12b. The third reference detection result relates to a position of the foreign object, a bounding box of the foreign object, a contour of the foreign object, a region of the foreign object, a dimension of the foreign object, a confidence value of the foreign object of the subject, or the like, or any combination thereof.

FIGS. 13a-16b illustrate exemplary detection results corresponding to one or more objects in an image determined based on a detection model according to some embodiments of the present disclosure.

Figure 13B:
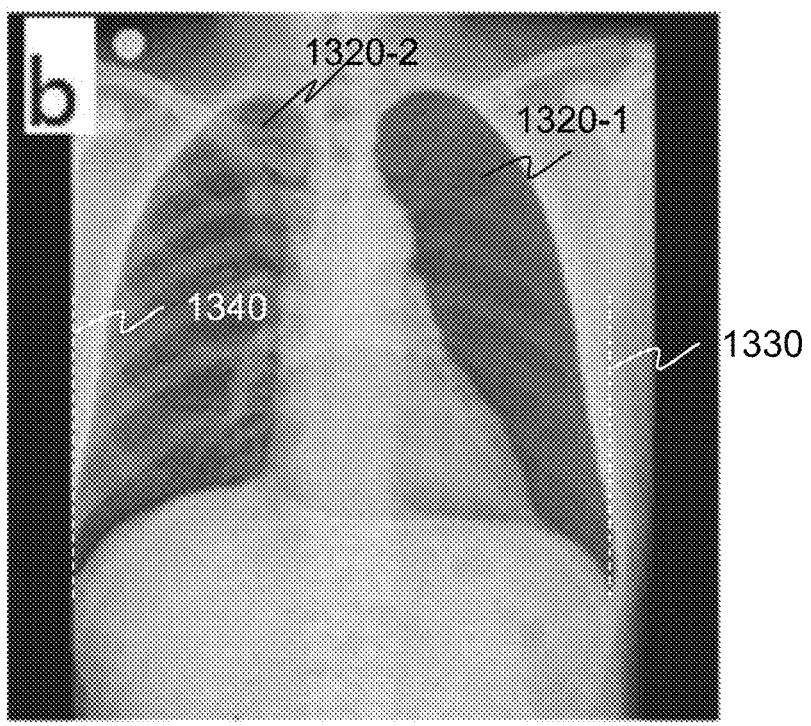
Figure 14A:
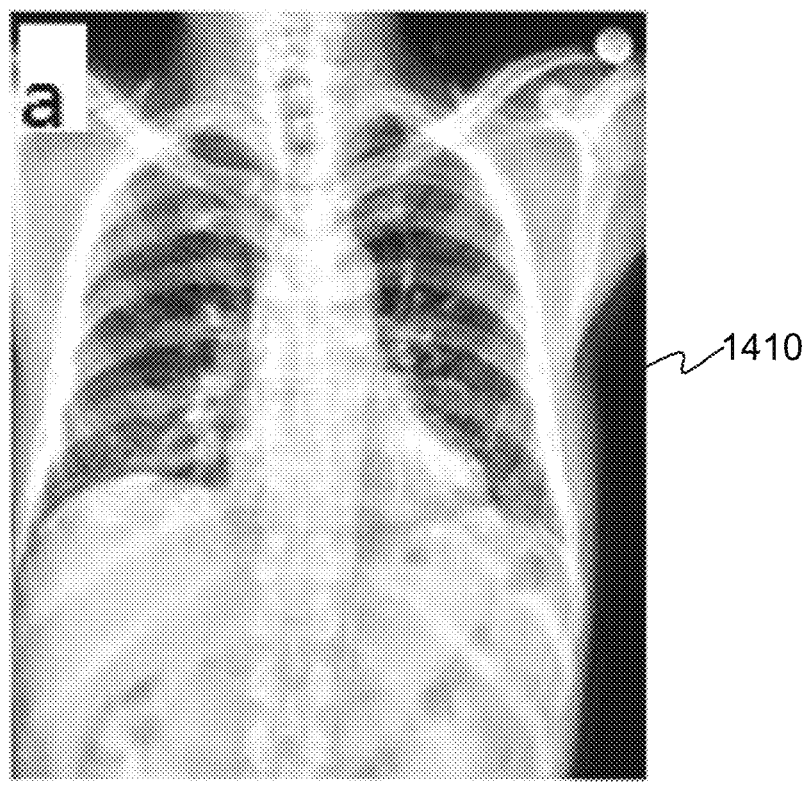
Figure 14B:
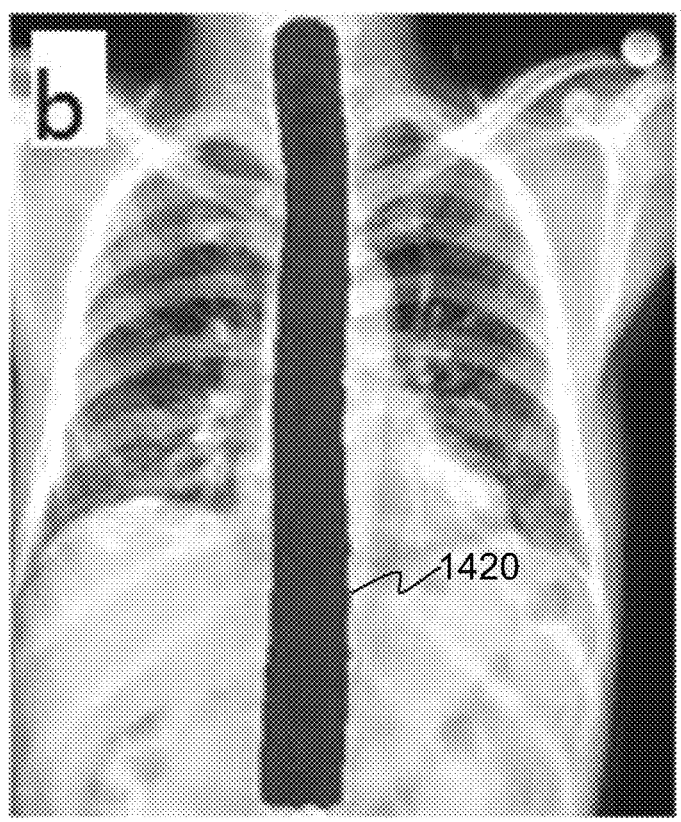
Figure 15A:
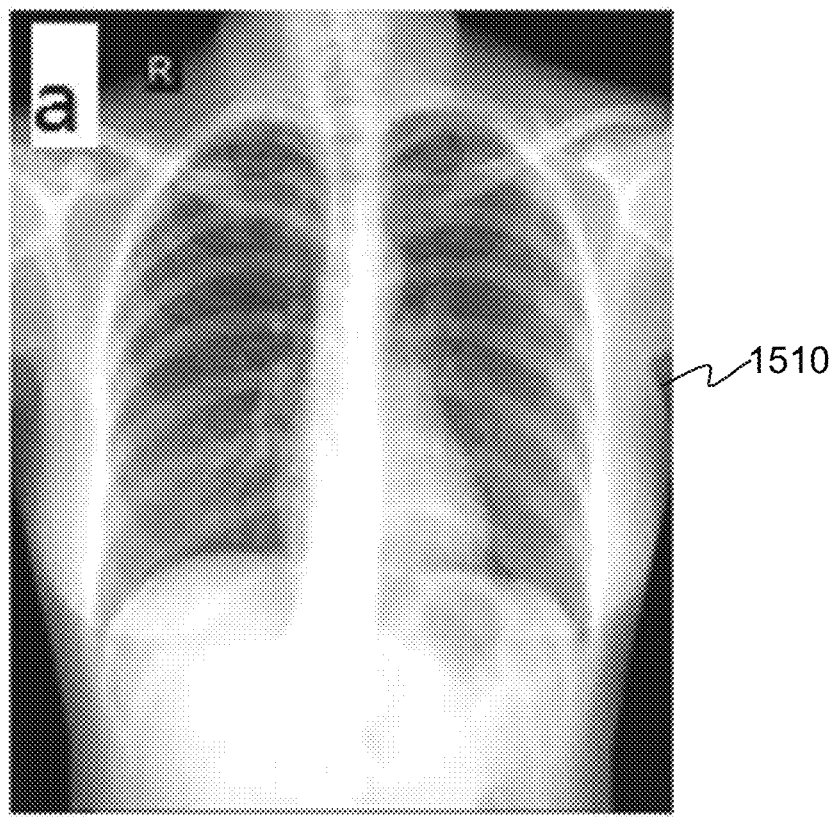
Figure 15B:
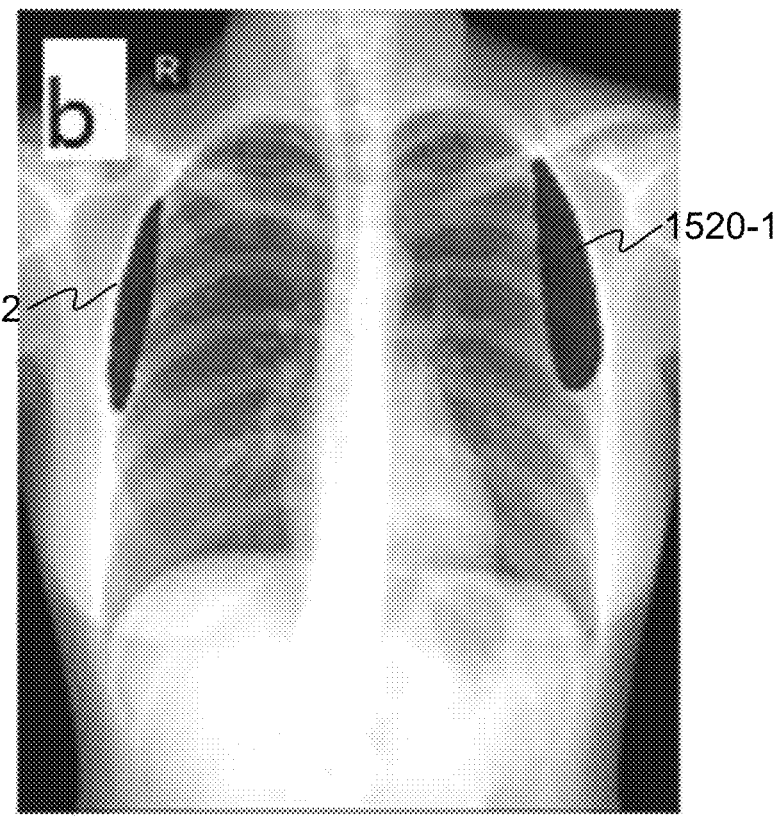
Figure 16A:
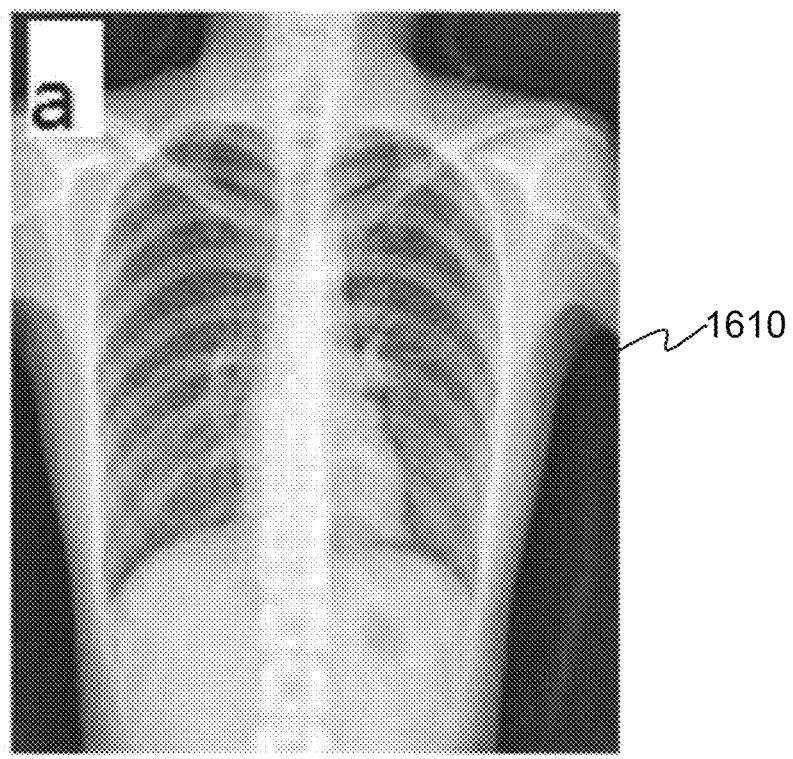
Figure 16B:
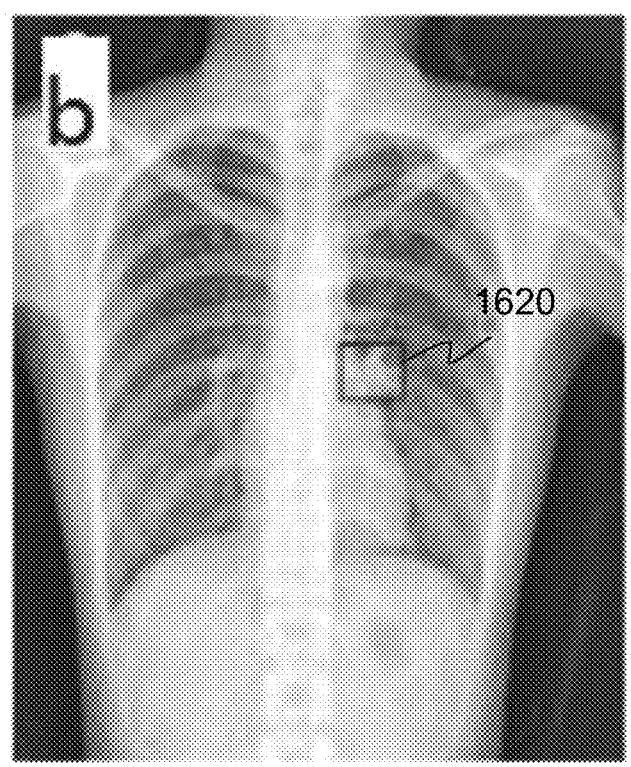

As illustrated in FIGS. 5-7, the processing device 140 may process the image of the subject using the detection model to generate the one or more detection results corresponding to the one or more objects in the image. Exemplary detection results may include a first detection result corresponding to a scapula, a second detection result corresponding to a lung, a third detection result corresponding to a foreign object, a fourth detection result corresponding to a spine, a fifth detection result corresponding to a heart, or the like, or any combination thereof. A region 1320-1 and a region 1320-2 may represent a second detection result corresponding to a lung of an image 1310 as shown in FIG. 13b. For instance, the second detection result relates to a position of the lung, a bounding box of the lung, a contour of the lung, a region of the lung, a dimension of the lung, or the like, or any combination thereof. A region 1420 may represent a fourth detection result corresponding to a spine of an image 1410 as shown in FIG. 14b. For instance, the fourth detection result relates to a position of the spine, a bounding box of the spine, a contour of the spine, a region of the spine, a dimension of the spine, or the like, or any combination thereof. A region 1520-1 and a region 1520-2 may represent a first detection result corresponding to a scapula of an image 1510 as shown in FIG. 15b. For instance, the first reference detection result relates to a position of the scapula, a bounding box of the scapula, a contour of the scapula, a region of the scapula, a dimension of the scapula of the subject, or the like, or any combination thereof. A region 1620 may represent a third reference detection result corresponding to a foreign object of an image 1610 as shown in FIG. 16b. For instance, the third detection result relates to a position of the foreign object, a bounding box of the foreign object, a contour of the foreign object, a region of the foreign object, a dimension of the foreign object, a confidence value of the foreign object of the subject, or the like, or any combination thereof.

Figure 17:
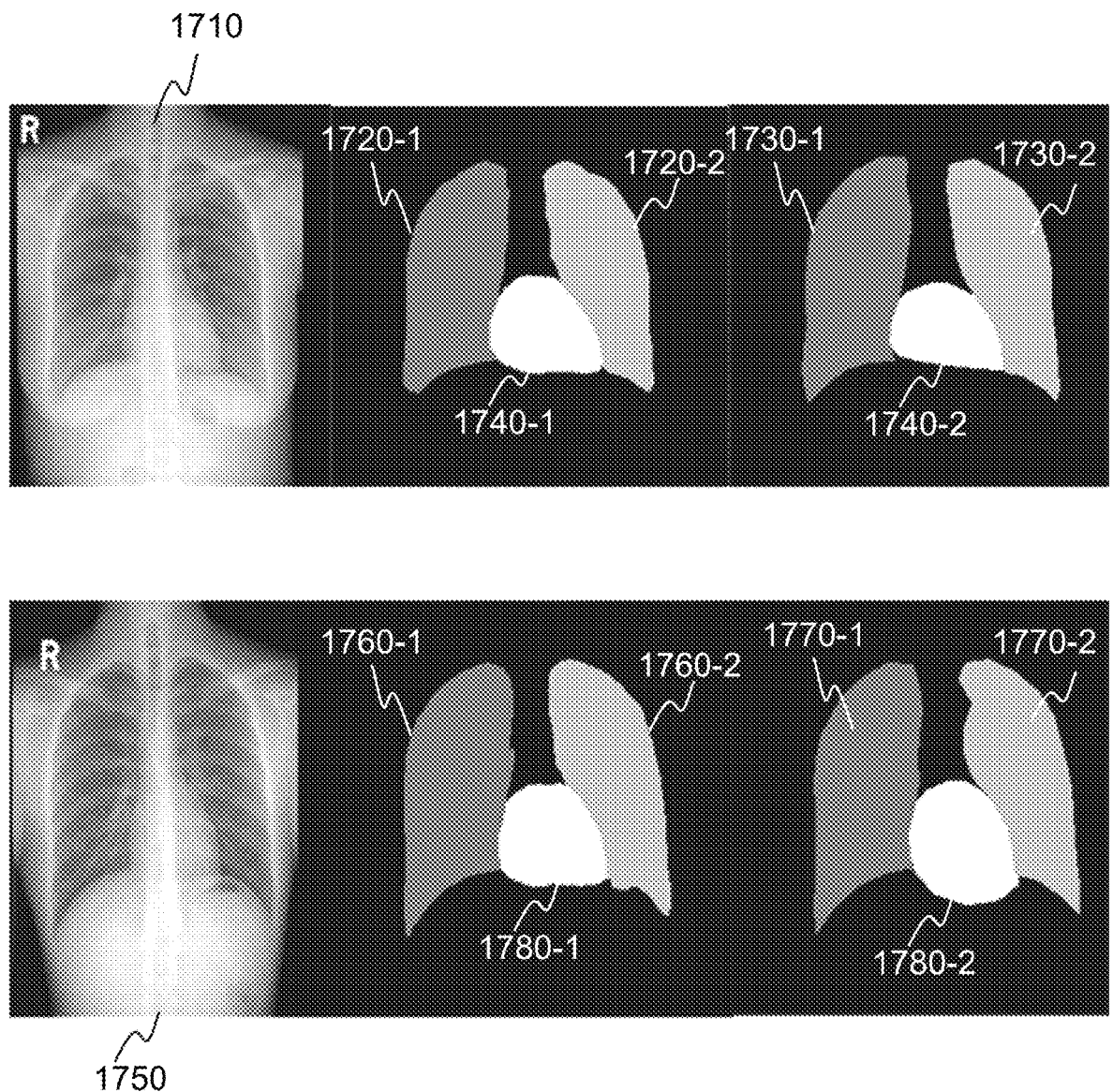
FIG. 17 illustrates exemplary reference detection results and detection results determined based on a detection model in an image according to some embodiments of the present disclosure.

FIG. 17 illustrates exemplary reference detection results and detection results determined based on a detection model in an image according to some embodiments of the present disclosure.

As shown in FIG. 17, a region 1720-1, a region 1720-2, and a region 1740-1 may represent a second detection result corresponding to a lung and a fifth detection result corresponding to a heart of an image 1710 determined based on the detection model as illustrated in FIGS. 4-8. A region 1730-1, a region 1730-2, and a region 1740-2 may represent a second reference detection result corresponding to the lung and a fifth reference detection result corresponding to the heart of the image 1710. For illustration purposes, the second reference detection result and the fifth reference detection result may be determined manually. A region 1760-1, a region 1760-2, and a region 1780-1 may represent a second detection result corresponding to a lung and a fifth detection result corresponding to a heart of an image 1750 determined based on the detection model as illustrated in FIGS. 4-8. A region 1770-1, a region 1770-2, and a region 1780-2 may represent a second reference detection result corresponding to the lung and a fifth reference detection result corresponding to the heart of the image 1750.

Figure 18:
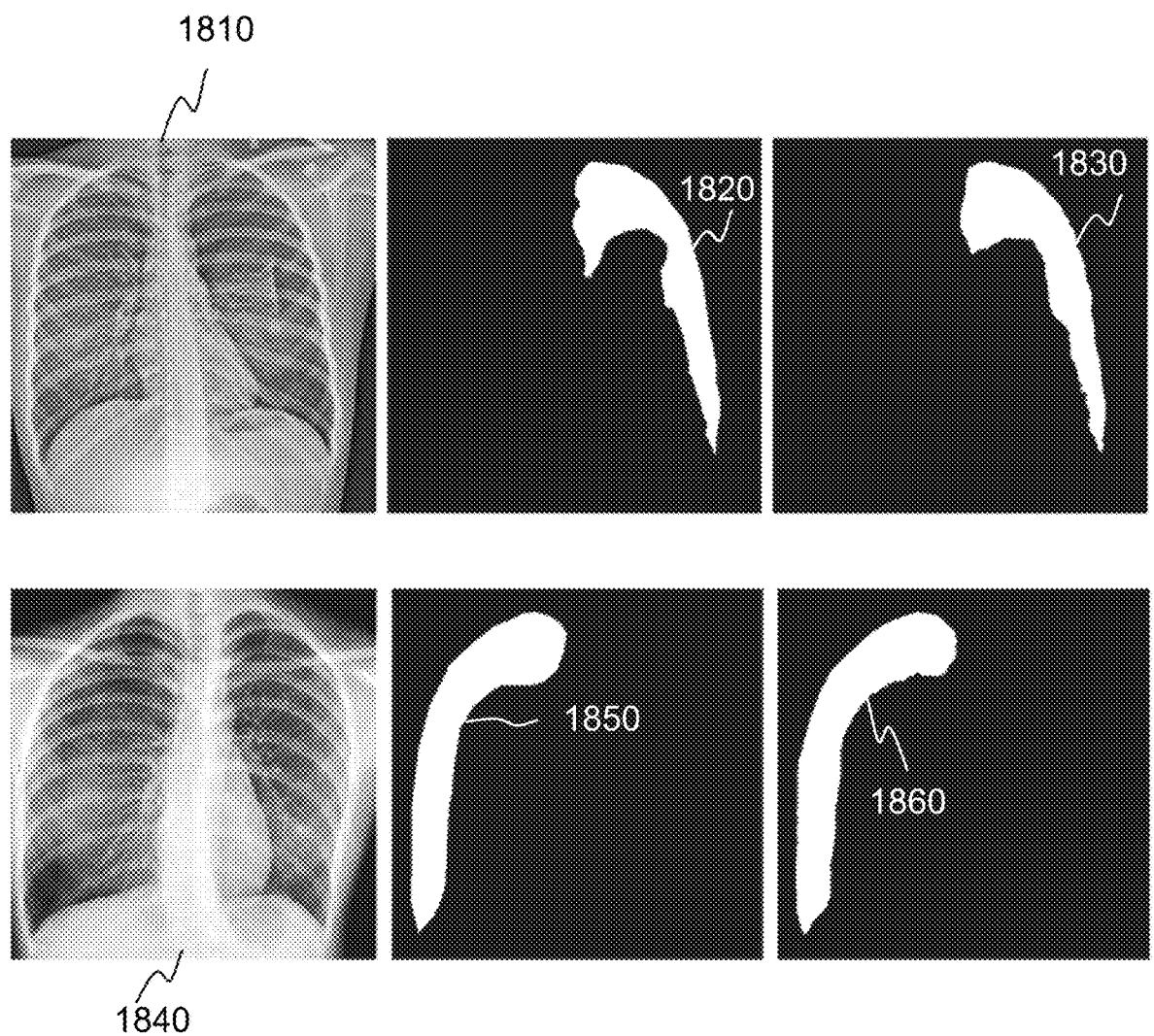
FIG. 18 illustrates an exemplary pathological condition in an image according to some embodiments of the present disclosure.

FIG. 18 illustrates an exemplary pathological condition in an image according to some embodiments of the present disclosure.

As shown in FIG. 18, a region 1820 may represent a reference sixth detection result corresponding to an abnormal part of an image 1810. A region 1830 may represent a sixth detection result corresponding to the abnormal part of the image 1810 determined based on the detection model as illustrated in FIGS. 4-8. A region 1850 may represent a reference sixth detection result corresponding to an abnormal part of an image 1840. A region 1860 may represent a sixth detection result corresponding to the abnormal part of the image 1840 determined based on the detection model as illustrated in FIGS. 4-8. The region 1820, 1830, 1850, and 1860 may be caused by pneumothorax.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device including a set of instructions;
at least one processor in communication with the at least one storage device, wherein when executing the set of instructions, the at least one processor is configured to cause the system to perform operations including:
processing an image of a subject using a detection model to generate one or more detection results corresponding to one or more objects in the image, the one or more objects comprising at least one of a lung, a spine, a scapula, a heart, a chest, a foreign object, an abnormal part, or a portion thereof, in the image;
generating a determination result by determining whether the one or more detection result corresponding to the one or more objects satisfy a condition, the condition comprising
an offset value of a detection result of the one or more detection results that corresponds to the spine relative to a reference line being smaller than or equal to an offset threshold, wherein the reference line includes a centerline of the image, and the offset value is defined by a total of distances between one or more points of the spine and a center point on the centerline of the image; and
generating an image metric of the image based on the determination result.

2. The system of claim 1, wherein
the one or more detection results corresponding to the one or more objects include at least one of
a position of one of the one or more objects in the image,
a bounding box of one of the one or more objects in the image,
a contour of one of the one or more objects in the image,
a region of the image that corresponds to one of the one or more objects in the image, or
a dimension of one of the one or more objects in the image.

3. The system of claim 1, wherein the condition also includes at least one of
a first ratio of a first area of a first detection result of the one or more detection results that corresponds to the scapula to a second area of a portion of the image that corresponds to the chest being smaller than or equal to a ratio threshold;
a second detection result of the one or more detection results that corresponds to the lung being located within a range of the image, wherein the range is defined by one or more distance thresholds between a boundary or contour of the lung and one or more edges of the image;

a second ratio of a third area of an overlapping region between the first detection result and the second detection result of the one or more detection results that corresponds to the lung to a fourth area of the second detection result being smaller than or equal to a second ratio threshold;

a third ratio of the third area to the second area being smaller than or equal to a third ratio threshold; or a confidence value of a third detection result of the one or more detection results that corresponds to the foreign object being smaller than or equal to a confidence value threshold.

4. The system of claim 3, wherein the image metric comprises an image quality classification that includes a first level and a second level, and the generating the image metric of the image based on the determination result includes:
determining the image quality classification based on the determination result.

5. The system of claim 4, wherein the determining the image quality classification based on the determination result includes:

in response to determining that the one or more detection results satisfy the condition, determining that the image belongs to the first level;

in response to determining that the second detection result satisfies the condition, that the third detection result fails to satisfy the condition, and that the third detection result is inside the second detection result, determining that the image belongs to the second level; or in response to determining that the second detection result fails to satisfy the condition, determining that the image belongs to the second level.

6. The system of claim 4, wherein the image quality classification further includes an intermediate level, and the determining the image quality classification based on the determination result includes:

in response to determining that the second detection result satisfies the condition, and that at least one of the detection result or the first detection result fails to satisfy the condition, determining that the image belongs to the intermediate level; or in response to determining that the second detection result satisfies the condition, that the third detection result fails to satisfy the condition, and that the third detection result is located outside the second detection result, determining that the image belongs to the intermediate level.

7. The system of claim 2, wherein the image metric comprises a clinical finding regarding at least one pathological condition including cardiac hypertrophy, pneumothorax, or pleural effusion, and the generating the image metric of the image based on the determination result includes:
in response to determining that the image belongs to a first level or an intermediate level, obtaining the clinical finding based on the one or more detection results corresponding to the one or more objects.

8. The system of claim 7, wherein the clinical finding relates to a pathological condition of cardiac hypertrophy, and the obtaining the clinical finding based on the one or more detection results corresponding to the one or more objects includes:

determining a fourth ratio of a width of one of the one or more detection results that corresponds to the heart to a width of the second detection result that corresponds to the lung;

comparing the fourth ratio with a fourth ratio threshold; and in response to determining that the fourth ratio exceeds the fourth ratio threshold, determining the clinical finding that the pathological condition of cardiac hypertrophy exists.

9. The system of claim 7, wherein the clinical finding relates to a pathological condition of pneumothorax, and the obtaining the clinical finding based on the one or more detection results corresponding to the one or more objects includes:

determining a fifth ratio of a count of elements of one of the one or more detection results that corresponds to the abnormal part to a count of elements of the second detection result; and determining, based on the fifth ratio, that a pathological condition of pneumothorax of high-risk pneumothorax or self-healing pneumothorax exists.

10. The system of claim 7, wherein the clinical finding relates to a pathological condition of pleural effusion, and the obtaining the clinical finding based on the one or more detection results corresponding to the one or more objects includes:

determining a sixth ratio of a count of elements of one of the one or more detection results that corresponds to the abnormal part to a count of elements of the second detection result; and determining, based on the sixth ratio, that a pathological condition of pleural effusion of high-risk pleural effusion or self-healing pleural effusion exists.

11. The system of claim 2, wherein the detection model includes at least one of a lung detection sub-model configured to determine a detection result corresponding to the lung in the image;

a spine detection sub-model configured to determine a detection result corresponding to a spine in the image;

a scapula detection sub-model configured to determine a detection result corresponding to the scapula in the image;

a foreign object detection sub-model configured to determine a detection result corresponding to the foreign object in the image;

an abnormal part detection sub-model configured to determine a detection result corresponding to the abnormal part in the image; or a heart detection sub-model configured to determine a detection result corresponding to the heart in the image.

12. The system of claim 1, wherein the at least one processor is configured to cause the system to perform the operations including:

preprocessing the image by performing at least one of
normalizing the image;
adjusting a size of the image;
rotating the image;
flipping the image;
cropping the image; or
changing a contrast ratio of the image.

13. The system of claim 1, wherein the detection model is generated by a training process comprising:
obtaining a plurality of training images; and
generating the detection model by training, based on the plurality of training images, a preliminary detection model.

14. The system of claim 13, wherein the obtaining a plurality of training images includes:
obtaining a plurality of first images;
generating a plurality of second images by:
adjusting a size of a first training object in each of at least a part of the plurality of first images;
rotating a second training object in each of at least a part of the plurality of first images;
filling a third training object in each of at least a part of the plurality of first images;
translating a fourth training object in each of at least a part of the plurality of first images;
flipping each of at least a part of the plurality of first images;
cropping each of at least a part of the plurality of first images; or
adjusting a contrast ratio of each of at least a part of the plurality of first images; and
determining the plurality of training image based on at least some of the plurality of first images and at least some of the plurality of second images.

15. The system of claim 1, the one or more detection results being used to determine a clinical finding regarding a pathological condition, wherein
the generating a determination result by determining whether the one or more detection result corresponding to the one or more objects satisfy a condition includes:
allocating one or more weights to the one or more detection results wherein the one or more weights relate to a type of the pathological condition; and
generating the determination result based on the one or more detection results corresponding to the one or more objects and the allocated one or more weights to the one or more detection results.

16. A method implemented on a computing device having at least one processor, at least one computer-readable storage medium, and a communication platform connected to a network, comprising:
processing an image of a subject using a detection model to generate one or more detection results corresponding to one or more objects in the image, the one or more objects comprising at least one of a lung, a spine, a scapula, a heart, a chest, a foreign object, an abnormal part, or a portion thereof, in the image;
generating a determination result by determining whether the one or more detection result corresponding to the one or more objects satisfy a condition, the condition comprising
an offset value of a fourth detection result of the one or more detection results that corresponds to the spine relative to a reference line being smaller than or equal to an offset threshold, wherein the reference line includes a centerline of the image, and the offset value is defined by a total of distances between one or more points of the spine and a center point on the centerline of the image; and
generating an image metric of the image based on the determination result.

17. The method of claim 16, wherein the image metric comprises a clinical finding regarding at least one pathological condition including cardiac hypertrophy, pneumothorax, or pleural effusion, and
the generating the image metric of the image based on the determination result includes:
in response to determining that the image belongs to a first level or an intermediate level, obtaining the clinical finding based on the one or more detection results corresponding to the one or more objects.

18. The method of claim 16, wherein the detection model is generated by a training process comprising:
obtaining a plurality of training images; and
generating the detection model by training, based on the plurality of training images, a preliminary detection model.

19. The method of claim 16, the one or more detection results being used to determine a clinical finding regarding a pathological condition, wherein
the generating a determination result by determining whether the one or more detection result corresponding to the one or more objects satisfy a condition includes:
allocating one or more weights to the one or more detection results wherein the one or more weights relate to a type of the pathological condition; and
generating the determination result based on the one or more detection results corresponding to the one or more objects and the allocated one or more weights to the one or more detection results.

20. A non-transitory computer readable medium, comprising:
instructions being executed by at least one processor, causing the at least one processor to implement a method comprising:
processing an image of a subject using a detection model to generate one or more detection results corresponding to one or more objects in the image, the one or more objects comprising at least one of a lung, a spine, a scapula, a heart, a chest, a foreign object, an abnormal part, or a portion thereof, in the image;
generating a determination result by determining whether the one or more detection result corresponding to the one or more objects satisfy a condition, the condition comprising
an offset value of a detection result of the one or more detection results that corresponds to the spine relative to a reference line being smaller than or equal to an offset threshold, wherein the reference line includes a centerline of the image, and the offset value is defined by a total of distances between one or more points of the spine and a center point on the centerline of the image; and
generating an image metric of the image based on the determination result.

* * * * *